(12) United States Patent
Kojima et al.

(10) Patent No.: US 9,772,314 B2
(45) Date of Patent: Sep. 26, 2017

(54) ULTRASONIC SENSOR AND MEASURING METHOD USING THE SAME, AND METHOD OF MANUFACTURING ULTRASONIC SENSOR

(71) Applicant: Seiko Epson Corporation, Tokyo (JP)

(72) Inventors: Chikara Kojima, Matsumoto (JP); Koji Ohashi, Shiojiri (JP)

(73) Assignee: Seiko Epson Corporation (JP)

( * ) Notice: Subject to any disclaimer, the term of this patent is extended or adjusted under 35 U.S.C. 154(b) by 278 days.

(21) Appl. No.: 14/573,011

(22) Filed: Dec. 17, 2014

(65) Prior Publication Data

US 2015/0177197 A1    Jun. 25, 2015

(30) Foreign Application Priority Data

Dec. 18, 2013  (JP) ................... 2013-261849
Nov. 18, 2014  (JP) ................... 2014-233351
Dec. 9, 2014   (JP) ................... 2014-249384

(51) Int. Cl.
*B06B 1/06*   (2006.01)
*G01L 9/08*   (2006.01)
(Continued)

(52) U.S. Cl.
CPC ....... *G01N 29/2437* (2013.01); *B06B 1/0674* (2013.01); *G01L 9/08* (2013.01);
(Continued)

(58) Field of Classification Search
CPC ......... G10K 11/28; G01L 9/08; B06B 1/0674; G01N 29/2437; G01N 29/221; G01N 2291/02872
(Continued)

(56) References Cited

U.S. PATENT DOCUMENTS 7,622,849 B2* 11/2009 Watanabe .............. G10K 9/122
                                                310/327
8,539,839 B2*  9/2013 Suzuki .................. B25J 13/082
                                                73/703
(Continued)

FOREIGN PATENT DOCUMENTS

EP       2666547 A2    11/2013
JP    2010-164331 A     7/2010
(Continued)

OTHER PUBLICATIONS

Extended European Search Report for Application No. EP 14 19 8884 dated Dec. 15, 2015 (9 pages).

*Primary Examiner* — J M Saint Surin
(74) *Attorney, Agent, or Firm* — Harness, Dickey & Pierce, P.L.C.

(57) ABSTRACT

An ultrasonic sensor which includes a substrate where an opening section is formed, a vibration plate that is provided on the substrate so as to close the opening section, and a piezoelectric element that is layered on a surface of the vibration plate on an opposite side to the opening section and includes a first electrode, a piezoelectric element, and a second electrode, includes a reflection layer that is provided in a space around the piezoelectric element on the surface of the vibration plate on an opposite side to the opening section, to reflect other ultrasonic waves which are transmitted in a different direction from a transmitted ultrasonic wave transmitted to a measuring target side on an interface between the piezoelectric element and the reflection layer, and has a thickness so as to superimpose other ultrasonic waves on the transmitted ultrasonic wave.

16 Claims, 17 Drawing Sheets

(51) Int. Cl.
 *G01N 29/22* (2006.01)
 *G01K 11/28* (2006.01)
 *G01N 29/24* (2006.01)
 *G10K 11/28* (2006.01)

(52) U.S. Cl.
 CPC .......... *G01N 29/221* (2013.01); *G10K 11/28* (2013.01); *G01N 2291/02872* (2013.01)

(58) Field of Classification Search
 USPC .............................. 73/627; 216/17; 427/100
 See application file for complete search history.

(56) References Cited

U.S. PATENT DOCUMENTS

| | | |
|---|---|---|
| 2007/0040477 A1 | 2/2007 | Sugiura et al. |
| 2011/0263982 A1 | 10/2011 | Kano |
| 2012/0247217 A1 | 10/2012 | Suzuki |
| 2014/0157902 A1* | 6/2014 | Sugiura ................ B06B 1/0666 73/627 |
| 2016/0282454 A1* | 9/2016 | Ohashi ................ B06B 1/0629 |

FOREIGN PATENT DOCUMENTS

| | | |
|---|---|---|
| JP | 2012-215533 A | 11/2012 |
| JP | 2015-097733 A | 5/2015 |
| WO | WO-2012-172775 A1 | 12/2012 |

* cited by examiner

FIG. 14
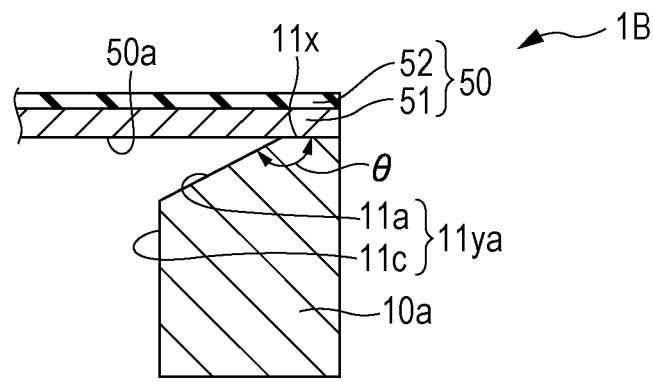
(a)
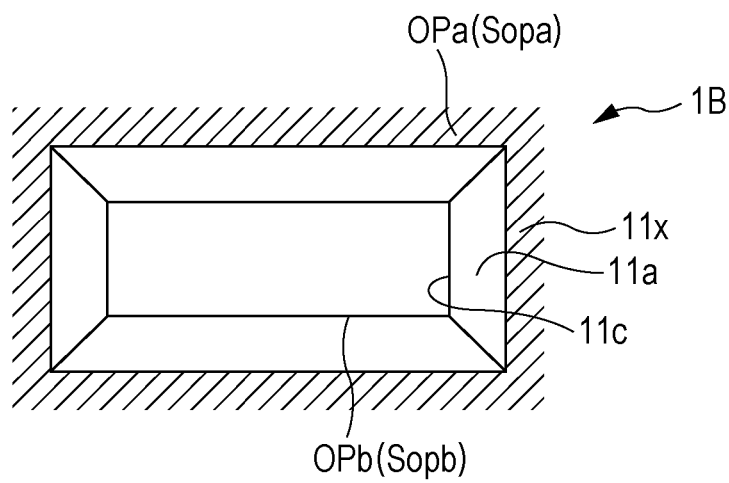
(b)
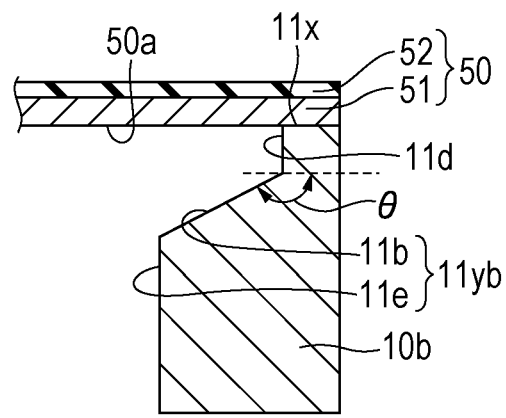
(c)

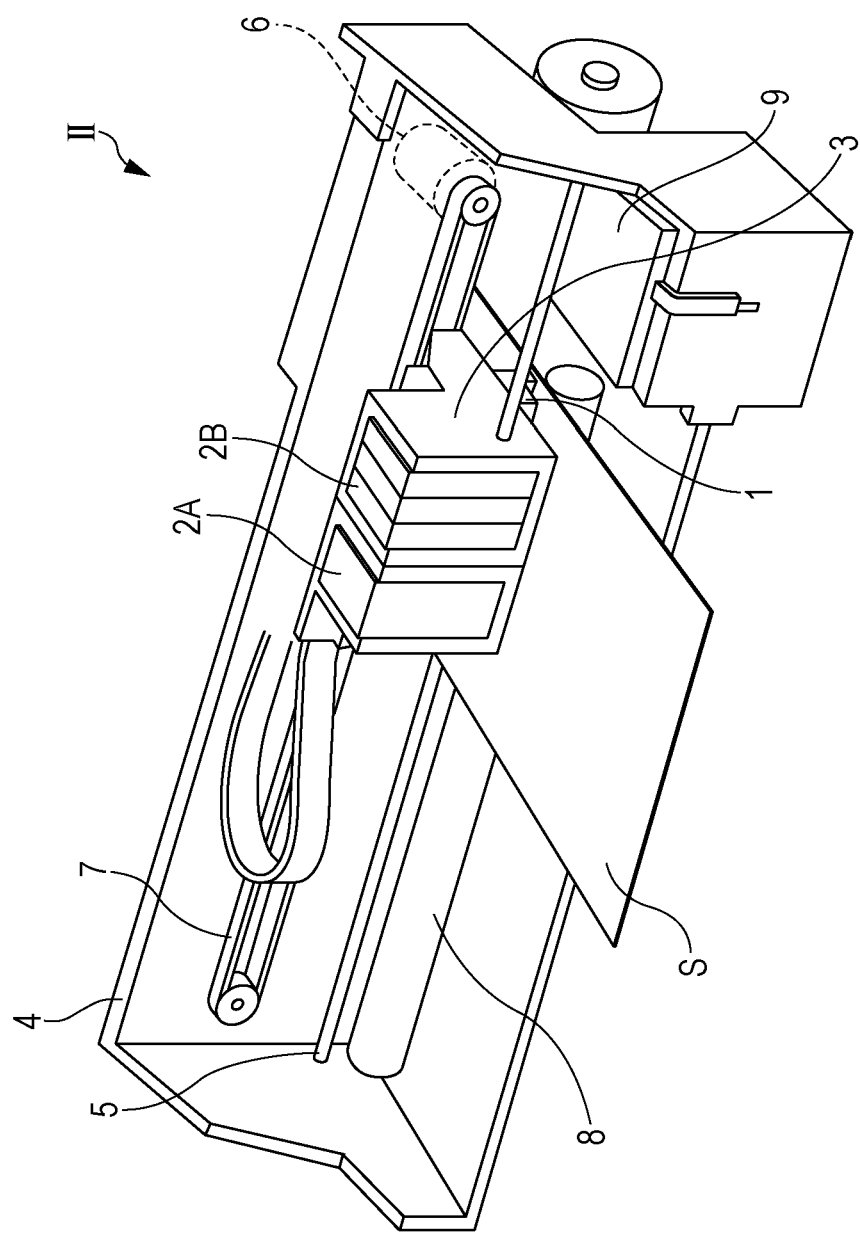

ULTRASONIC SENSOR AND MEASURING METHOD USING THE SAME, AND METHOD OF MANUFACTURING ULTRASONIC SENSOR

BACKGROUND

1. Technical Field

The present invention relates to an ultrasonic sensor and a measuring method using the same, and a method for manufacturing an ultrasonic sensor.

2. Related Art

Hitherto, an ultrasonic sensor is known as one of a detector for obtaining various information relating to a measuring target. On the basis of the time that is from the time of transmitting an ultrasonic wave until the time of receiving an echo signal which is generated in such a manner that the transmitted ultrasonic wave is reflected on the measuring target and comes back, the ultrasonic sensor obtains the information relating to a position, a shape, and speed of the measuring target.

As an ultrasonic sensor of such kind, for example, an ultrasonic sensor that includes a control calculation section which calculates the position, the shape, and the speed of a detection target (measuring target), on the basis of the ultrasonic wave transmitted from an ultrasonic sensor unit having a vibration plate and a piezoelectric material, and the ultrasonic wave reflected by the detection target and received by the ultrasonic sensor unit, and covers the periphery of the piezoelectric material by a reflection chamber, is known (for example, see JP-A-2010-164331). In addition, as the ultrasonic sensor of such kind, for example, an ultrasonic sensor that includes a support in which an opening section is formed; a support film which is provided to close the opening section; a piezoelectric material (piezoelectric element) which is provided on the side opposite to the support of the support film; and a frame which is provided around the piezoelectric element, and further includes a sealing film sealing the piezoelectric element, in which a space sealed by the sealing film (space including the piezoelectric element) is filled with silicone oil as a pressure medium, and is applied as a pressure sensor, is known (for example, see JP-A-2012-215533 (FIG. 3(B) or the like)).

However, in the ultrasonic sensor of JP-A-2010-164331, there is a case of generating other ultrasonic waves which are transmitted in a different direction from the ultrasonic wave transmitted to the measuring target side. For that reason, with respect to all of the generated ultrasonic waves, there is a case that a ratio of the ultrasonic wave transmitted to the measuring target side becomes low. If the propagation efficiency of the ultrasonic wave transmitted to the measuring target side is not sufficient, there is a possibility that various information relating to the measuring target may not be accurately obtained. In addition, in JP-A-2012-215533 (FIG. 3(B) or the like), since the space including the piezoelectric element is filled with the silicone oil, there is a case of generating a leakage current via the silicone oil during driving of the piezoelectric element. In this case, there is a possibility that it becomes difficult to improve detection accuracy including capability (distance resolution) to separate and identify a measuring target.

Furthermore, such problems are similarly present in not only the ultrasonic sensors of JP-A-2010-164331 and JP-A-2012-215533, but also, for example, the ultrasonic sensor that has the vibration plate and the piezoelectric material, and generates other ultrasonic waves which are transmitted in the different direction from the ultrasonic wave transmitted to the measuring target side.

The present invention is made by considering the above-described situations, and object thereof is to provide an ultrasonic sensor that can improve propagation efficiency of an ultrasonic wave and a measuring method using the same, and a method for manufacturing an ultrasonic sensor.

SUMMARY

According to an aspect of the invention for solving the above-described problems, there is provided an ultrasonic sensor which includes a substrate where an opening section is formed, a vibration plate provided on the substrate so as to close the opening section, and a piezoelectric element provided on a surface of the vibration plate on an opposite side to the opening section, the piezoelectric element having a first electrode, a piezoelectric material layer, and a second electrode. The sensor further includes a reflection layer provided in a space around the piezoelectric element on the surface of the vibration plate on an opposite side to the opening section, to reflects other ultrasonic waves which are transmitted in a different direction from a transmitted ultrasonic wave transmitted to a measuring target side on an interface between the piezoelectric element and the reflection layer. The reflection layer has a thickness so as to superimpose other ultrasonic waves on the transmitted ultrasonic wave.

According to the aspect, it is possible to superimpose other ultrasonic waves which are transmitted in the different direction (for example, opposite direction) from the transmitted ultrasonic wave transmitted to the measuring target side on the transmitted ultrasonic wave, and enlarge an amplitude thereof. Accordingly, it is possible to increase strength of the transmitted ultrasonic wave, and improve the propagation efficiency of the ultrasonic wave.

In the aspect, the reflection layer can be configured as an air layer. When the reflection layer is configured as an air layer, it is possible to remarkably reduce the leakage current during driving of the piezoelectric element, in comparison with a case where an acoustic matching layer (silicone oil or the like) is provided on a region around the piezoelectric element. Accordingly, it is possible to prevent adverse effects from a detection of a measuring target, as a result, it is possible to improve the detection accuracy including capability (distance resolution) to separate and identify the measuring target. Furthermore, since the leakage current is remarkably reduced as described above, the ultrasonic sensor becomes an excellent ultrasonic sensor in electrical safety. In addition, according the aspect, since the substrate is attached to an opposite side to the piezoelectric element of the vibrating plate, the processing of the opening section is facilitated.

Here, it is preferable that an acoustic impedance ratio of the reflection layer to the piezoelectric element is three times or more. According thereto, it is possible to suitably reflect other ultrasonic waves on the interface between the reflection layer and the piezoelectric element. Therefore, it is possible to surely improve the propagation efficiency of the ultrasonic wave.

Moreover, it is preferable that the reflection layer has acoustic impedance which is smaller than the acoustic impedance of the piezoelectric element. According thereto, it is possible to widen selectivity of a configuration material of the above reflection layer. Consequently, it is possible to improve the propagation efficiency of the ultrasonic wave, and increase a freedom degree of the configuration of the ultrasonic sensor.

Additionally, it is preferable that a space is secured on the piezoelectric element, and the reflection layer is made up of an air layer that is formed between the piezoelectric element, and an enveloping plate which is formed on the vibration plate so as to envelop the piezoelectric element and the space. According thereto, it is possible to easily form the reflection layer, and protect the piezoelectric element by the enveloping plate. Accordingly, it is possible to easily configure the ultrasonic sensor that improves the propagation efficiency of the ultrasonic wave, and enhance structure stability of the ultrasonic sensor. Furthermore, since the leakage current can be remarkably reduced during driving of the piezoelectric element, it is possible to improve the detection accuracy. Furthermore, when the piezoelectric element is configured as a thin film, availability for handling thereof can be improved, and thus, the ultrasonic sensor is easily manufactured and handled.

Furthermore, it is preferable that the space is secured on the piezoelectric element, and the reflection layer is made up of a resin composition layer that is inserted between the piezoelectric element, and an enveloping plate which is formed on the vibration plate so as to envelop the piezoelectric element and the space. According thereto, it is possible to easily form the reflection layer of the different acoustic impedance, and protect the piezoelectric element by the enveloping plate. Therefore, it is possible to easily configure the ultrasonic sensor that improves the propagation efficiency of the ultrasonic wave, and enhance the structure stability of the ultrasonic sensor.

Moreover, it is preferable that other ultrasonic waves that are reflected on the interface between the reflection layer and the piezoelectric element, have a phase difference which is greater than 0 degree, and is 120 degrees or less, with respect to the transmitted ultrasonic wave. According thereto, it is possible to enlarge the amplitude of the ultrasonic wave depending on the phase difference. Thus, it is possible to improve the propagation efficiency of the ultrasonic wave.

Additionally, it is preferable that the thickness of the piezoelectric element is 0.4 µm to 2.0 µm. According thereto, it is possible to decrease a time gap from the time of generating other ultrasonic waves, until the time of reflecting the other ultrasonic waves on the interface between the reflection layer and the piezoelectric element, and propagating the other ultrasonic waves to the measuring target side. Therefore, the other ultrasonic waves are likely to be superimposed on the transmitted ultrasonic wave, and the other ultrasonic waves are unlikely to interfere with an echo signal on the measuring target side. Consequently, it is possible to improve the propagation efficiency of the ultrasonic wave, and enhance measuring resolving power.

Moreover, it is preferable that the thickness of the vibration plate is 0.5 µm to 3.0 µm. According thereto, it is possible to decrease the time gap from the time of generating other ultrasonic waves, until the time of reflecting the other ultrasonic waves on the interface between the reflection layer and the piezoelectric element, and propagating the other ultrasonic waves to the measuring target side. Therefore, the other ultrasonic waves are likely to be superimposed on the transmitted ultrasonic wave, and the other ultrasonic waves are unlikely to interfere with the echo signal on the measuring target side. Consequently, it is possible to improve the propagation efficiency of the ultrasonic wave, and enhance the measuring resolving power.

In addition, according to another aspect of the invention, there is provided an ultrasonic sensor including: a vibration plate that including a first surface and a second surface; a piezoelectric element that is provided on the first surface of the vibration plate and including a first electrode, a piezoelectric material layer, and a second electrode; a substrate that is attached to the second surface of the vibration plate and including an opening section at a position facing the piezoelectric element; and an acoustic matching layer that is provided in a space formed by the opening section and the second surface of the vibration plate, to propagate an ultrasonic wave generated by driving of the piezoelectric element; and an air layer provided in a region around the piezoelectric element is set as an air layer.

According to the aspect, since the region opposite to the vibrating plate and the opening section of the piezoelectric element is set as the air layer, the leakage current during driving of the piezoelectric element can be remarkably reduced in comparison with a case where the acoustic matching layer is provided in the region around the piezoelectric element. Accordingly, it is possible to prevent adverse effects from a detection of a measuring target, as a result, it is possible to improve the detection accuracy including capability (distance resolution) to separate and identify the measuring target. Furthermore, since the leakage current is remarkably reduced as described above, the ultrasonic sensor becomes an excellent ultrasonic sensor in electrical safety. In addition, according the aspect, since the substrate is attached to an opposite side to the piezoelectric element of the vibrating plate, the processing of the opening section is facilitated.

It is preferable that the substrate includes a first wall surface that is provided in parallel to the second surface of the vibration plate and is joined with the second surface, and a second wall surface partitioning the opening section, the second wall surface includes a vertical wall perpendicular to the first wall surface and an inclined wall that is provided between the first wall surface and the second wall surface and is inclined to the first and second wall surfaces, and an angle formed by the inclined wall and the second surface of the vibration plate is equal to or greater than 90 degrees. According to this, an area of an opening of the vibrating plate side can be increased more than the area of an opening of the other side by varying the opening area in the opening section in a thickness direction. Therefore, a contact area between the vibrating plate and the acoustic matching layer increases. Accordingly, it is possible to reduce the area in which displacement of the vibrating plate is restrained by the substrate, and to increase an operating region of the vibrating plate. By increasing the contact area between the vibrating plate and the acoustic matching layer, and the operating region of the vibrating plate, it is possible to suitably absorb a residual vibration due to the vibration plate, even if the residual vibration is generated in the acoustic matching layer. That is, the acoustic matching layer is configured to exhibit a function as a so-called damper, therefore, it possible to reduce the residual vibration in the acoustic matching layer. As a result, it is possible to further improve the detection accuracy including the distance resolution. Specifically, when the ultrasonic sensor is configured such that two or more units of the ultrasonic sensor which is configured with a smallest unit consisting of one piezoelectric element and one opening section, are provided, a partition wall is formed by the substrate between the opening sections of the adjacent units. According to this, by providing the partition wall between the adjacent opening sections, it is possible to block the residual vibration propagating the acoustic matching layer, and to suppress the vibration attenuation of adjacent elements. As a result, it is possible to further improve the detection accuracy including distance resolution.

In addition, it is preferable that the ultrasonic sensor includes a circuit that transmits and receives drive signals to and from the piezoelectric element, in which the circuit transmits and receives the drive signals for resonating the piezoelectric element in a resonant mode. According to this, it is possible to transmit an ultrasonic wave having high strength by largely displacing the piezoelectric element and the vibration plate by using resonance. In addition, by largely displacing the piezoelectric element and the vibration plate based on a reflected ultrasonic wave from the measuring target, it is possible to obtain electric signals having high strength. According to this, since detection using the electrical signals having high strength is possible, it is possible to further improve the detection accuracy including distance resolution.

According to another aspect of the invention for solving the above-described problems, there is provided a measuring method using an ultrasonic sensor which includes a substrate where an opening section is formed, a vibration plate that is provided on the substrate so as to close the opening section, and a piezoelectric element having a first electrode, a piezoelectric material layer, and a second electrode layered on the vibration plate, the method including, reflecting other ultrasonic waves which are transmitted in a different direction from a transmitted ultrasonic wave transmitted to a measuring target side, by a reflection layer that is provided on an opposite side to the opening section of the vibration plate, and superimposing the other ultrasonic waves on the transmitted ultrasonic wave.

According to the aspect, it is possible to superimpose the other ultrasonic waves which are transmitted in the different direction (for example, opposite direction) from the transmitted ultrasonic wave transmitted to the measuring target side on the transmitted ultrasonic wave, and enlarge the amplitude thereof. Accordingly, it is possible to increase the strength of the transmitted ultrasonic wave, and improve the propagation efficiency of the ultrasonic wave.

According to a still another aspect of the invention for solving the above-described problems, there is provided a method for manufacturing an ultrasonic sensor, the method including: preparing a substrate; forming a vibration plate including a first surface and a second surface on the substrate; forming a piezoelectric element including a first electrode, a piezoelectric material layer, and a second electrode on the first surface of the vibration plate; forming an opening section at a position facing the piezoelectric element of the substrate; providing an acoustic matching layer propagating an ultrasonic wave generated by driving of the piezoelectric element in a space formed by the opening section and the second surface of the vibration plate; and setting a region around the piezoelectric element as an air layer.

According to the aspect, since the region opposite to the vibration plate and the opening section of the piezoelectric element is manufactured as the air layer, the ultrasonic sensor can be remarkably reduce the leakage current during driving of the piezoelectric element in comparison with a case where an acoustic matching layer is provided in a region around the piezoelectric element. Accordingly, it is possible to prevent adverse effects from a detection of a measuring target, as a result, it is possible to improve the detection accuracy including capability (distance resolution) to separate and identify the measuring target. Furthermore, since the leakage current is remarkably reduced as described above, the ultrasonic sensor becomes an excellent ultrasonic sensor in electrical safety. In addition, according the aspect, since the substrate is attached to an opposite side to the piezoelectric element of the vibrating plate, the processing of the opening section is facilitated.

In addition, it is preferable that the forming of the opening section includes forming a vertical wall by etching the substrate so as to be perpendicular to the second surface of the vibration plate, and forming an inclined wall so as to be inclined to the second surface of the vibration plate and the vertical wall, and so as to be equal to or greater than 90 degrees of an angle with respect to the second surface. According to this, an area of the opening section of the vibrating plate side can be increased more than the area of an opening of the other side by varying the opening area in the opening section in a thickness direction. Therefore, the contact area between the vibrating plate and the acoustic matching layer increases. Accordingly, it is possible to reduce the area in which the displacement of the vibrating plate is restrained by the substrate, and to increase an operating region of the vibrating plate. By increasing the contact area between the vibrating plate and the acoustic matching layer, and the operating region of the vibrating plate, it is possible to suitably absorb a residual vibration by the vibration plate, even if the residual vibration is generated in the acoustic matching layer. That is, the acoustic matching layer is configured to exhibit a function as a so-called damper, therefore, it possible to reduce the residual vibration in the acoustic matching layer. As a result, it is possible to further improve the detection accuracy including distance resolution. Specifically, when the ultrasonic sensor is configured that two or more units of the ultrasonic sensor which is configured with a smallest unit including one piezoelectric element and one opening section are provided, a partition wall is formed by the substrate between the opening sections of the adjacent units. According to this, by providing the partition wall between the adjacent opening sections, it is possible to block the residual vibration propagating the acoustic matching layer, and to suppress the vibration attenuation of adjacent elements. As a result, it is possible to further improve the detection accuracy including distance resolution.

In addition, it is preferable that an enveloping plate enveloping the piezoelectric element and the air layer is further provided on the first surface of the vibration plate. According to this, since the air layer is secured in the region around the piezoelectric element, and the piezoelectric element can be physically protected, it is possible to improve the detection accuracy including distance resolution. Therefore, it is possible to further improve the manufacturing strength of the ultrasonic sensor having excellent electrical safety. Furthermore, when the piezoelectric element is configured as a thin film, the availability for handling thereof can be improved, and thus, the ultrasonic sensor is easily manufactured and handled.

BRIEF DESCRIPTION OF THE DRAWINGS

FIGS. 14(a)-(c) are enlarged cross-sectional views of the ultrasonic sensor according to Embodiment 3, a plan view which is viewed from a first wall surface side, and an enlarged cross-sectional view of the ultrasonic sensor according to the modification example, respectively.

FIG. 18 is a diagram illustrating a schematic configuration of a liquid ejecting apparatus according to one embodiment of the invention.

DESCRIPTION OF EXEMPLARY EMBODIMENTS

Figure 1:
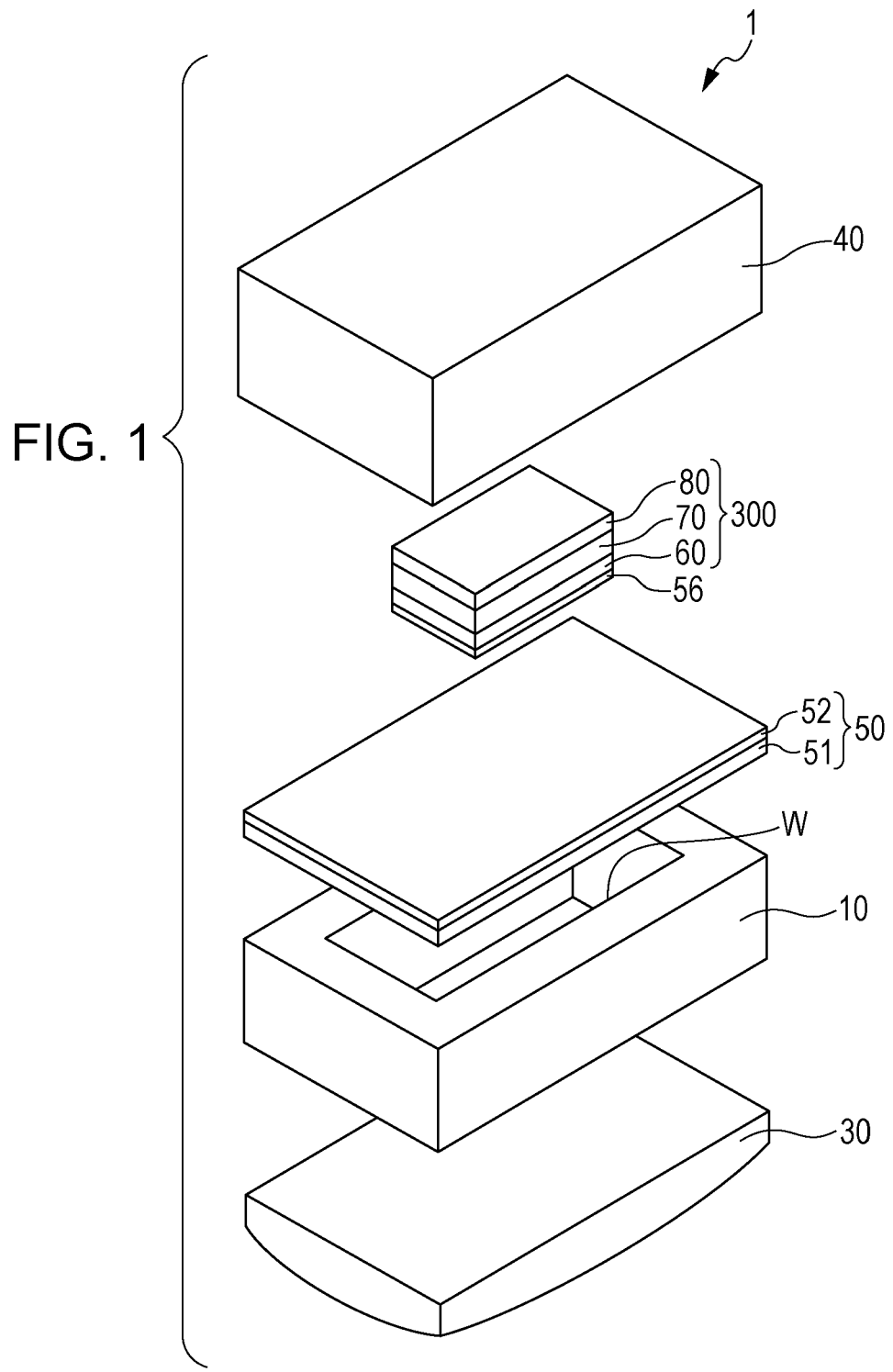
FIG. 1 is an exploded perspective view illustrating a schematic configuration of an ultrasonic sensor according to Embodiment 1.

Embodiments of the invention will now be described by way of example only with reference to the drawings. However, the following description is a way to describe an aspect of the invention, and it can be modified arbitrarily within the scope of the present invention. In the drawings, components having practically the same function are represented by the same reference numerals, and the description thereof will not be repeated.

Embodiment 1

Embodiment 1 of the invention relates to an ultrasonic sensor including a reflection layer that is to reflect other ultrasonic waves which are transmitted in a different direction from a transmitted ultrasonic wave transmitted to a measuring target side on an interface between a piezoelectric element and the reflection layer, and has a thickness so as to superimpose the other ultrasonic waves on the transmitted ultrasonic wave.

Figure 2:
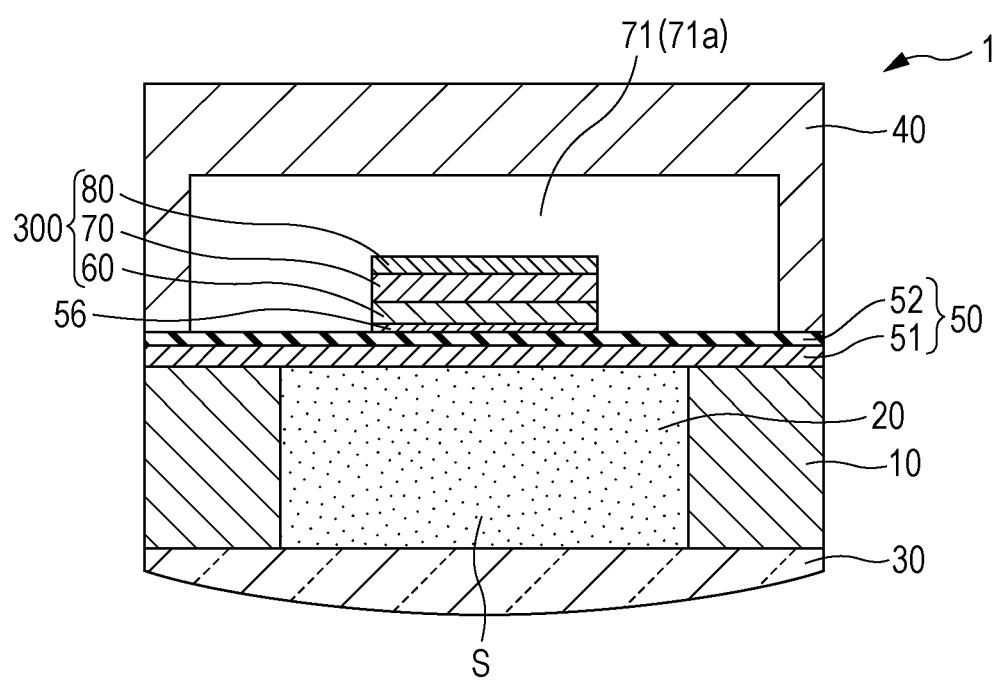
FIG. 2 is a cross-sectional view of the ultrasonic sensor according to Embodiment 1.

FIG. 1 is an exploded perspective view illustrating a schematic configuration of the ultrasonic sensor according to Embodiment 1 of the invention, and FIG. 2 is a cross-sectional view when the ultrasonic sensor of FIG. 1 is cut along a width direction.

As shown in the drawings, an ultrasonic sensor 1 includes a substrate 10 where an opening section W is formed, a vibration plate 50 that is provided on the substrate 10 so as to close the opening section W, and a piezoelectric element 300 that is made up of a first electrode 60, a piezoelectric material layer 70, and a second electrode 80 which are layered on the vibration plate 50.

In the substrate 10, for example, a silicon (Si) single crystal substrate can be used, and the vibration plate 50 can be configured, for example, as an elastic film 51 which is made up of silicon dioxide (SiO2), and an insulator film 52 which is made up of zirconium oxide or the like. The piezoelectric element 300 is bent and deformed by voltage application to the piezoelectric element 300, and an ultrasonic wave is generated, depending on displacement of the piezoelectric element 300 and the vibration plate 50 due thereto. The insulator film 52 can be omitted.

In the embodiment, the opening section W is assumed to be a passage region of the ultrasonic wave (simply referred to as "transmitted ultrasonic wave," hereinafter) which is transmitted to a measuring target side, and the piezoelectric element 300 is formed on an opposite side to the opening section W of the vibration plate 50. According thereto, a configuration of the opposite side to the piezoelectric element 300 of the vibration plate 50, is simplified, and it is possible to secure the favorable passage region of the ultrasonic wave. Moreover, an electrical region such as electrode and wiring, and an adhered and fixed region of each member, are kept away from the measuring target, and it is easy to prevent contamination and leakage current between the regions and the measuring target.

Accordingly, the embodiment becomes the ultrasonic sensor 1 that can be suitably used as a pressure sensor which is mounted on a printer, needless to say, and can be suitably used for a medical device in situations averse to the contamination and a leakage current in particular from a point of safety or the like, for example, an ultrasonic diagnostic apparatus, a sphygmomanometer, and a tonometer.

Furthermore, in the embodiment, a space is secured on the piezoelectric element 300 (an upper face and a side face of the piezoelectric element 300), and an enveloping plate 40 which is formed on the vibration plate 50 so as to envelop the piezoelectric element 300 and the space, but the enveloping plate 40 may be omitted. However, by providing the enveloping plate 40, since the piezoelectric element 300 is physically secured, and strength of the ultrasonic sensor 1 is also increased, it is possible to enhance structure stability. Still more, when the piezoelectric element 300 is configured as a thin film, availability of the ultrasonic sensor 1 including the piezoelectric element 300 for handling, can be improved. For example, the enveloping plate 40 can be configured of a silicon-based material, and if the silicon-based material is also used in the substrate 10 and the vibration plate 50, it is possible to join each section by the same kind of material.

On the opposite side to the vibration plate 50 of the substrate 10, a lens member 30 which is permeable for the ultrasonic wave or the like, is provided. In a space S which is formed by the lens member 30, the substrate 10, and the vibration plate 50, a predetermined resin composition is inserted, and an acoustic matching layer 20 is formed. According thereto, it is possible to prevent a rapid acoustic impedance change between the piezoelectric element 300 and the measuring target. If there is no need to converge the ultrasonic wave, it is possible to omit the lens member 30 or provide a lid member closing the opening section W in place of the lens member 30.

That is, when the acoustic impedance is rapidly changed between the piezoelectric element 300 and the measuring target, the ultrasonic wave is reflected on an interface without propagating through the interface thereof. On the other hand, the acoustic impedance is changed in stages between the piezoelectric element 300 and the measuring target by the acoustic matching layer 20, and thereby, the reflection of the ultrasonic wave which is caused by rapidly changing the acoustic impedance between the piezoelectric element 300 and the measuring target, can be prevented, and the ultrasonic wave is efficiently propagated to the measuring target side.

Moreover, in the embodiment, the configuration of a minimum unit where there is one opening section W on the substrate 10, is employed, and it becomes an advantageous mode for miniaturization. However, a number of minimum units on the substrate 10 may be provided in parallel one-dimensionally in a width direction or a length direction, or may be provided in parallel two-dimensionally in the width direction or the length direction. In this case, it is possible to use a number of detection signals in order to obtain various information relating the measuring target, and it is possible to improve reliability.

When the ultrasonic sensor 1 is provided in parallel one-dimensionally or two-dimensionally, after configuring the individual ultrasonic sensor 1, they may be configured to be connected and fixed, or the vibration plate, the lens member, or the like may be used as a common member, using the substrate where the opening sections W are plurally formed.

On the opposite side to the opening section W of the vibration plate 50, an insulator film 52 that is made up of zirconium oxide or the like, and an adhesion layer 56 that improves adhesion properties with a ground of the first electrode 60 which has a thickness of approximately 30 nm to 50 nm and is made up of titanium oxide or the like, are provided. The insulator film 52 and the adhesion layer 56 may be omitted as necessary. On the adhesion layer 56, the piezoelectric element 300 which is made up of the first electrode 60, the piezoelectric material layer 70, and the second electrode 80, is formed. Here, the piezoelectric element 300 may be used as a portion including the first electrode 60, the piezoelectric material layer 70, and the second electrode 80.

Generally, in the piezoelectric element 300, any one of the electrodes is used as a common electrode, and the other electrode and the piezoelectric material layer 70 are configured by patterning per opening section W. Accordingly, in the case of the mode where the ultrasonic sensor 1 is provided in parallel one-dimensionally or two-dimensionally, for example, the first electrode 60 may be used as a common electrode of the piezoelectric element 300, and the second electrode 80 may be used as an individual electrode of the piezoelectric element 300, but even if reversed for convenience of a drive circuit or the wiring, there is no trouble.

Here, the piezoelectric element 300, and the vibration plate 50 where the displacement is generated by the drive of the piezoelectric element 300, may be altogether referred to as an actuator apparatus. In the above example, the vibration plate 50, the insulator film 52 and the adhesion layer 56 which are provided as necessary, and the first electrode 60 operate as a vibration plate, but are not limited thereto. For example, instead of providing the vibration plate 50, the piezoelectric element 300 itself may be made so as to substantially serve a function as a vibration plate.

If the first electrode 60 and the second electrode 80 have conductivity, the first electrode 60 and the second electrode 80 are not limited. For example, metal materials such as platinum (Pt), iridium (Ir), gold (Au), aluminum (Al), copper (Cu), titanium (Ti), and stainless steel, tin oxide-based conductive material such as indium tin oxide (ITO), and fluorine-doped tin oxide (FTO), oxide conductive materials such as zinc oxide-based conductive material, strontium ruthenate (SrRuO3), lanthanum nickelate (LaNiO3), and element doped strontium titanate, conductive polymer or the like, may be used. However, the first electrode 60 and the second electrode 80 are not limited to the materials.

In the piezoelectric material layer 70, complex oxide of a lead zirconate titanate (PZT)-based perovskite structure, may be representatively used. According thereto, it is easy to secure a displacement amount of the piezoelectric element 300. Moreover, in the piezoelectric material layer 70, the material which does not include lead, for example, the complex oxide of a so-called BF-BT-based perovskite structure including at least bismuth (Bi), barium (Ba), iron (Fe), and titanium (Ti) or the complex oxide of a so-called KNN-based perovskite structure including at least potassium (K), sodium (Na), and niobium (Nb), may be used. According thereto, it is possible to realize the ultrasonic sensor 1, using nonlead-based materials of which load to environment is small.

In such a perovskite type structure, in the A site of an $ABO_3$ type structure, oxygen is coordinated as 12, and in the B site, oxygen is coordinated as 6, and an eight-sided body (octahedron) is made. In the example of the piezoelectric material layer 70 by the BF-BT-based materials, Bi, Ba and Li are positioned in the A site, and Fe and Ti are positioned in the B site.

In the example of the BF-BT-based materials, a composition formula thereof is expressed by $(Bi, Ba)(Fe, Ti)O_3$, but as a representative composition, it is expressed by a mixed crystal of bismuth ferrate and barium titanate. Such mixed crystal refers to a mixed crystal where bismuth ferrite or barium titanate can not be detected alone by an X-ray diffraction pattern. The composition which deviates from the composition of the mixed crystal, is also included. On the other hand, in the example of the so-called KNN-based materials, K and Na are placed in an A site and Nb is placed in a B site. The composition formula thereof is represented by $(K, Na)NbO_3$.

Here, in the complex oxide of the perovskite structure, the complex oxide which deviates from the composition of stoichiometry due to loss or excess, and the complex oxide where a portion of the element is substituted to other elements, are also included. That is, as long as the perovskite structure can be adopted, an inevitable deviation of the composition due to lattice mismatch, oxygen deficiency or the like, needless to say, and portion substitution of the element, are allowed.

For example, it is preferable that the complex oxide of the BF-BF-based or KNN-based perovskite structure further includes manganese (Mn). According thereto, it is easy to suppress the leakage current, and for example, it is possible to realize the ultrasonic sensor 1 of which reliability is high as a nonlead-based material.

Examples of the additive other than manganese (Mg) in the above BF-BT-based materials include lithium (Li), samarium (Sm), or cerium (Ce) which is substituted with a part of Bi in the A site of the piezoelectric material layer 70, or aluminum (Al) or cobalt (Co) which is substituted with a part of Fe in the B site. In addition, examples of the addictive other than Mn in the KNN-based materials include lithium (Li), barium (Ba), calcium (Ca), strontium (Sr), zirconium (Zr), titanium (Ti), bismuth (Bi), tantalum (Ta), antimony (Sb), iron (Fe), cobalt (Co), silver (Ag), magnesium (Mg), zinc (Zn), copper (Cu), or the like. The addictive may include one or more. Generally, an amount of the addictive is 15% or less with respect to a total amount of the elements serving as a main component. By using the addictive, it is easy to configure the piezoelectric material layer 70 so that various kinds of properties are improved, and achieve diversification of the functions. Even in the case of the complex oxide including other elements, it is preferable that the complex oxide is configured so as to have the perovskite structure.

Figure 3:
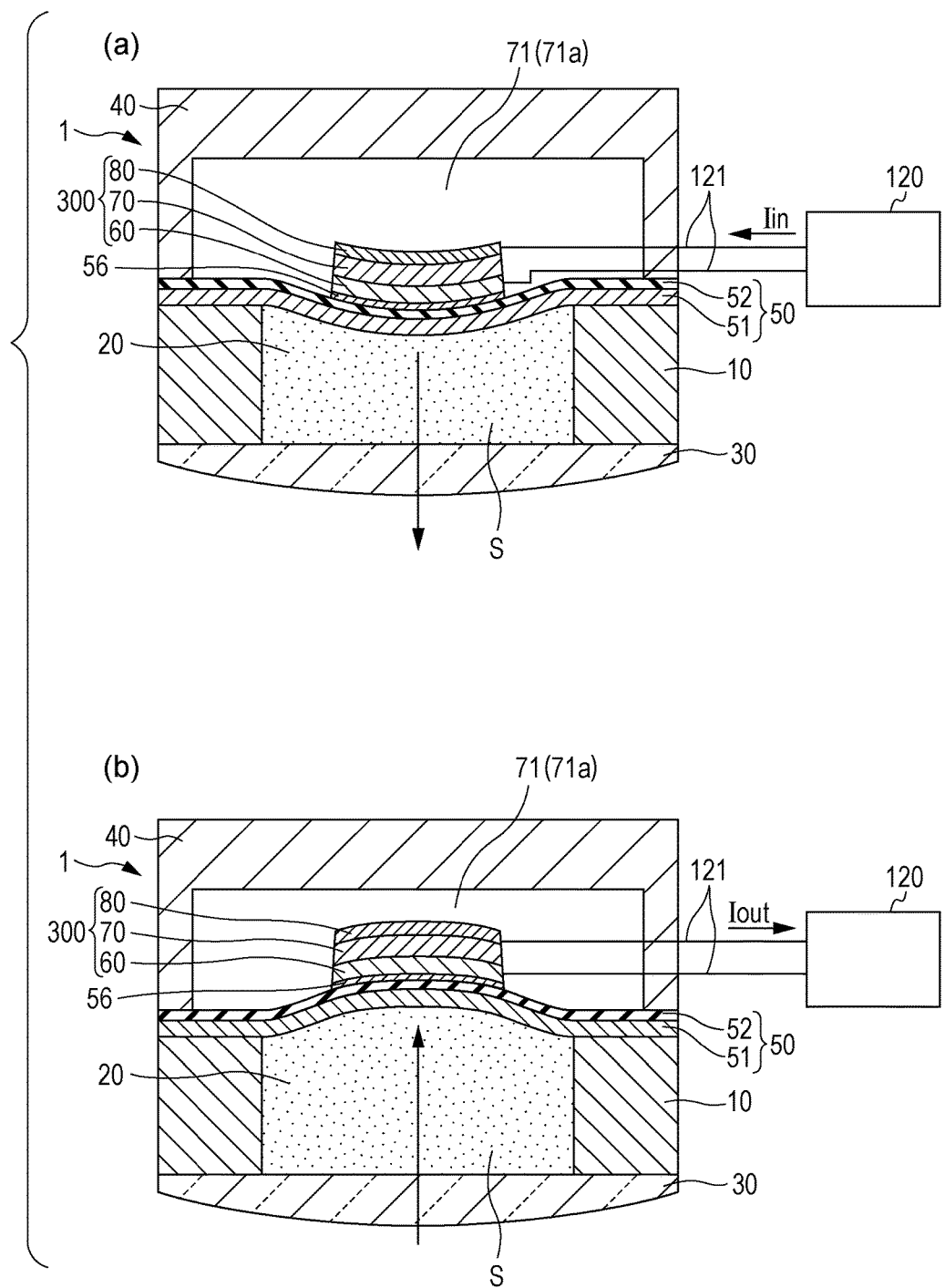
FIGS. 3(a) and (b) are diagrams illustrating a motion of the ultrasonic sensor according to Embodiment 1.

The piezoelectric element 300 described above, is bent and deformed by the voltage application from a circuit (24 which is shown in FIG. 3). Since a tendency of the bent deformation of the piezoelectric element 300 is changed by the configuration materials, the thicknesses, arrangement, size or the like of the piezoelectric element 300 and the vibration plate 50, the tendency can be appropriately adjusted depending on an intended use and a use mode. Using a peculiar resonance frequency of each material, the resonance frequency is agreed with a frequency of a charge signal which is applied to the piezoelectric element 300, or is substantially agreed therewith, and the piezoelectric element 300 may be bent and deformed using the resonance.

As a result of the bent deformation of the piezoelectric element 300, the piezoelectric element 300 and the vibration plate 50 are displaced, and for example, the transmitted ultrasonic wave to the measuring target side is generated, depending on the displacement. Specifically, as shown in FIG. 3(a), a charge signal Iin is applied to the piezoelectric element 300 through a wiring 121 from the circuit 120, and the piezoelectric element 300 is bent and deformed with the piezoelectric material layer 70 which is interposed between the first electrode 60 and the second electrode 80 and is substantially a drive section, as a center thereof. As a result, the piezoelectric element 300 and the vibration plate 50 are displaced, and an ultrasonic wave is generated and transmitted to the measuring target side (downward side in the drawing) is generated.

As described above, in the embodiment, the configuration that the opposite side to the piezoelectric element 300 of the vibration plate 50 becomes the passage region of the ultrasonic wave, is employed, and the favorable passage region of the ultrasonic wave is secured. Moreover, the electrical region such as electrode and wiring, and the adhered and fixed region of each member, are kept away from the measuring target, and it is easy to prevent the contamination and the leakage current between the regions and the measuring target.

The circuit 120 can be appropriately configured in combination with a control unit (not shown) which is configured with a known power supply apparatus (not shown) or a known micro computer as the center. The circuit 120 can be connected and fixed to the first electrode 60 and the second electrode 80, and hereby, the structure stability and the electrical reliability are improved. However, within the scope of the invention as defined by the claims, the circuit in which the first electrode 60 and the second electrode 80 are electrically separable, may be configured, and hereby, maintenance or repair exchange becomes easy. Additionally, it is possible to simplify the configuration of the ultrasonic sensor 1 itself.

In the case where there is the measuring target, the ultrasonic wave transmitted to the measuring target side, is reflected on the measuring target, and comes back to the ultrasonic sensor 1 side. As shown in FIG. 3(b), the ultrasonic wave which is reflected on the measuring target, is incident on the vibration plate 50 as an echo signal, and according thereto, the vibration plate 50 and the piezoelectric element 300 are displaced, and a generated charge signal $I_{out}$ is measured by the circuit 120. Therefore, in the control unit which is not shown in the drawing, on the basis of a time gap between the charge signal $I_{in}$ and the charge signal $I_{out}$, calculation is performed, and a position, a shape and speed of the measuring target are detected.

In the ultrasonic sensor 1 using the displacement of the piezoelectric element 300 and the vibration plate 50, there is a case of generating other ultrasonic waves which are transmitted in a different direction (for example, the opposite side to the measuring target) from the transmitted ultrasonic wave to the measuring target side. Thereupon, in the embodiment, an region 71 that other ultrasonic waves which are transmitted in the different direction from the transmitted ultrasonic wave, are reflected on the interface between the piezoelectric element 300 and a reflection layer, and has the thickness so as to superimpose other ultrasonic waves on the transmitted ultrasonic wave, is included on the opposite side to the opening section W of the vibration plate 50. The region serves as a reflection layer 71 according to the embodiment.

The reflection of the ultrasonic wave by the reflection layer 71, is performed on the basis of an acoustic impedance ratio on the interface between the reflection layer 71 and the piezoelectric element 300. Accordingly, it is preferable that the acoustic impedance ratio of the reflection layer 71 to the piezoelectric element 300 is three times or more. According thereto, the other ultrasonic waves can be suitably reflected on the interface between the reflection layer 71 and the piezoelectric element 300, and the propagation efficiency of the ultrasonic wave can be surely improved.

Such reflection layer 71 is favorable, if the acoustic impedance ratio of the reflection layer 71 to the piezoelectric element 300 is a predetermined value or more. The reflection layer 71 may have acoustic impedance which is greater than the acoustic impedance of the piezoelectric element 300, and the reflection layer 71 may have the acoustic impedance which is smaller than the acoustic impedance of the piezoelectric element 300. In this way, the configuration material of the reflection layer 71 can be appropriately selected, depending on the configuration of the piezoelectric element 300.

For example, the reflection layer 71 can be configured so as to be made up of an air layer 71a which is formed between the piezoelectric element 300 and the enveloping plate 40. It is known that the acoustic impedance of the air is approximately $4.3 \times 10^{-4}$ MRaly. Moreover, when the piezoelectric element 300 is configured from the first electrode 60, the piezoelectric material layer 70, and the second electrode 80, for example, there are many cases where the acoustic impedance thereof is, approximately 0.7 MRaly ($1.0 \times 10^{-6}$ kg·m$^{-2}$·s$^{-1}$). At this time, if a reflectance R which is expressed by the following formula (1), is calculated, the reflectance R is approximately 0.998, and on the interface between the piezoelectric element 300 and the air layer 71a, approximately 99.8% of the ultrasonic wave is reflected, that is, it is found that the ultrasonic wave is nearly not propagated.

$$\text{Reflectance } R=(Z_0-Z_1)/(Z_0+Z_1) \quad (1)$$

($Z_0$: the acoustic impedance of the piezoelectric element, $Z_1$: the acoustic impedance of the air layer)

Accordingly, by including the reflection layer 71 which is made up of the air layer 71a, the reflection layer 71 can be formed more easily. Furthermore, it is possible to have the above effect in which the piezoelectric element 300 can be protected by the enveloping plate 40.

Figure 4:
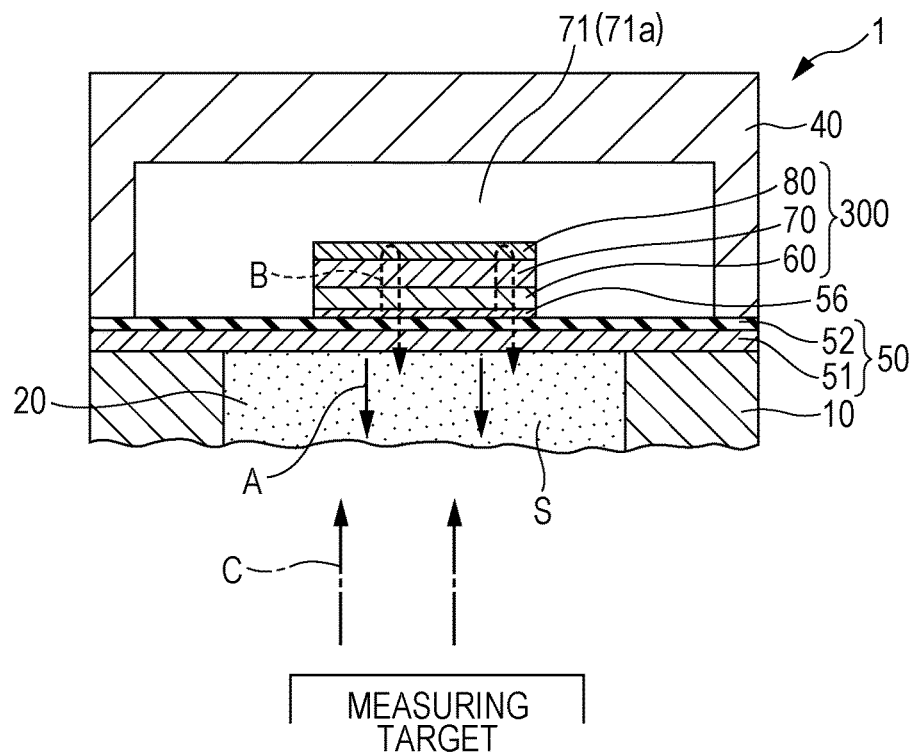
FIG. 4 is a diagram illustrating the motion of the ultrasonic sensor according to Embodiment 1.

The ultrasonic sensor 1 of the embodiment will be described in more detail, using FIG. 4. FIG. 4 is an enlarged cross-sectional view of the ultrasonic sensor 1 of the embodiment. In the drawing, the ultrasonic wave transmitted to the measuring target side is shown by a solid line arrow A, other ultrasonic waves which are reflected by the reflection layer 71 and are transmitted to the measuring target side, are shown by a dashed line arrow B, and the echo signal which is reflected on the measuring target, is shown by a dot and dash line arrow C.

In the ultrasonic sensor 1, the piezoelectric element 300 is bent and deformed by the voltage application in the direction of the opening section W, and as a result, the piezoelectric element 300 and the vibration plate 50 are displaced, and an ultrasonic wave A transmitted to the measuring target side, is generated.

On the other hand, depending on the bent deformation of the piezoelectric element 300, there is the case where the ultrasonic wave is generated in the different direction from the measuring target side. For example, on the opposite side to the measuring target side, there is the case where another ultrasonic wave B is generated. Since the ultrasonic sensor 1 includes the reflection layer 71, the other ultrasonic wave B is reflected on the interface between the reflection layer 71 and the piezoelectric element 300, and a transmitting direction thereof is changed, and the other ultrasonic wave B is transmitted to the measuring target side.

Here, in the embodiment, it is preferable that the thickness of the piezoelectric element 300 is 0.4 μm to 2.0 μm. Moreover, it is preferable that the thickness of the vibration plate 50 is 0.5 μm to 3.0 μm. If the piezoelectric element 300 and the vibration plate 50 are relatively thin as described above, in comparison with the case where the piezoelectric element 300 and the vibration plate 50 are relatively thick, for example, the case where the piezoelectric element is a bulk, it is possible to shorten a propagation distance until the other ultrasonic wave B arrives at the interface between the reflection layer 71 and the piezoelectric element 300, and it is possible to shorten the propagation distance until the other ultrasonic wave B, which is reflected on the interface, arrives at the measuring target side. Hence, the time gap from the time of generating the other ultrasonic wave B until the time of reflecting the other ultrasonic wave B on the interface between the reflection layer 71 and the piezoelectric element 300, and propagating the other ultrasonic wave B to the measuring target side, can be small. Accordingly, it is possible to suitably superimpose the other ultrasonic wave B on the transmitted ultrasonic wave A.

Figure 5:
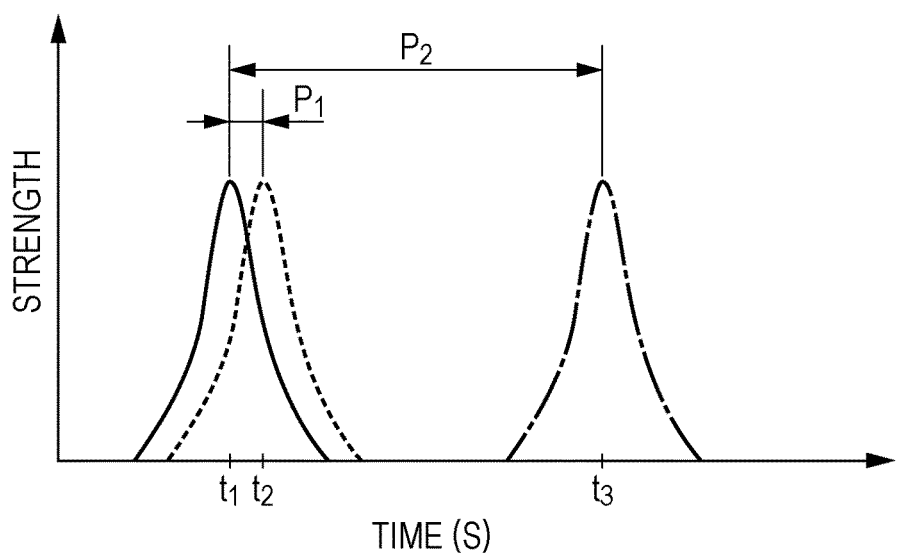
FIG. 5 is a graph describing an ultrasonic waveform of the ultrasonic sensor according to Embodiment 1.

FIG. 5 is a time chart illustrating amplitude of the transmitted ultrasonic wave A, the other ultrasonic wave B, and an echo signal C. As shown in FIG. 5, in the embodiment, a period $P_1$ which is from a time $t_1$ of generating the transmitted ultrasonic wave A until a time $t_2$ of overlapping the other ultrasonic wave B with the transmitted ultrasonic wave A, is shorter than a period $P_2$ which is from the time $t_1$ of generating the transmitted ultrasonic wave A until a time $t_3$ of receiving the echo signal C.

In this way, if the piezoelectric element 300 and the vibration plate 50 are relatively thin as described above, although there is the difference depending on the distance to the measuring target, it is possible to prevent the echo signal C from being incident before the other ultrasonic wave B is superimposed on the transmitted ultrasonic wave A, and a possibility that the other ultrasonic wave B interferes with the echo signal C, becomes extremely low.

Figure 6:
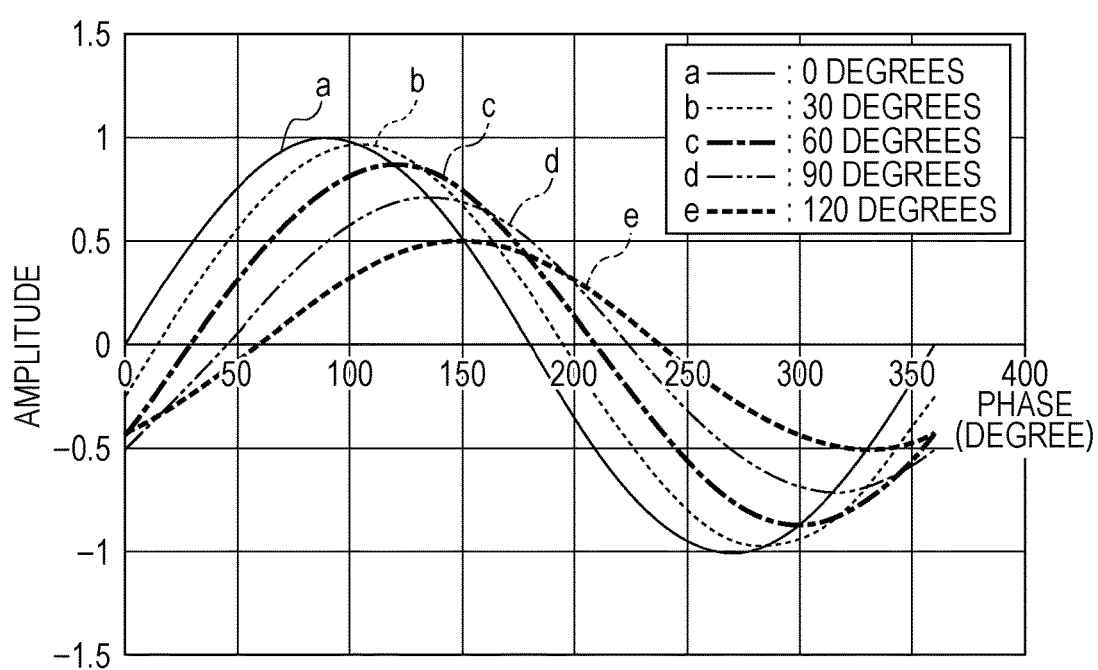
FIG. 6 is a graph describing the ultrasonic waveform of the ultrasonic sensor according to Embodiment 1.

A phase difference between the transmitted ultrasonic wave A and the other ultrasonic wave B, can be appropriately selected within the scope of the invention as defined by the appended claims, if the other ultrasonic wave B does not interfere with the echo signal C, and the value does not have a bad influence on the amplitude of the transmitted ultrasonic wave A. FIG. 6 is a diagram describing a change of the amplitude when the transmitted ultrasonic wave A and the other ultrasonic wave B are superimposed.

As shown in the drawing, theoretically, if a phase difference both of the transmitted ultrasonic wave A and the other ultrasonic wave B is 0 degree, waveforms thereof are completely agreed, the amplitude is doubled, and it is possible to improve the strength thereof. If the piezoelectric element 300 and the vibration plate 50 are relatively thin as described above, since the propagation distance until the other ultrasonic wave B is reflected on the interface between the reflection layer 71 and the piezoelectric element 300, and arrives at the measuring target side, can be short, it becomes easy to reduce the real phase difference between both the transmitted ultrasonic wave A and the other ultrasonic wave B.

For example, it is preferable that a delay until the other ultrasonic wave B is superimposed on the transmitted ultrasonic wave A, is ⅓ or less of the period of the transmitted ultrasonic wave A, in other words, that the other ultrasonic wave B has the phase difference which is greater than 0 degree, and is 120 degrees or less, with respect to the transmitted ultrasonic wave A, and it is more preferable that the other ultrasonic wave B has the phase difference which is greater than 0 degree, and is 60 degrees or less. According thereto, the other ultrasonic wave B does not have the bad influence on the amplitude of the transmitted ultrasonic wave A. Moreover, the amplitude of the ultrasonic wave is enlarged by the phase difference, and the propagation efficiency can be improved more.

As an example, the case where a frequency of the transmitted ultrasonic wave A is approximately 7.5 MHz, will be described. In this case, the period of the transmitted ultrasonic wave A is approximately $1.3 \times 10^{-7}$s, from a reciprocal number of the frequency of the transmitted ultrasonic wave A. Moreover, density of the piezoelectric element 300 is approximately $2 \times 10^3$ kg/m$^3$, ultrasonic wave speed within the piezoelectric element 300, that is, the speed of sound is approximately $1 \times 10^3$ m/s, a film thickness of the piezoelectric element 300 is 1 μm, and propagation time (delay) of the other ultrasonic wave B is 1 μm/$1 \times 10^3$ m/s=1 ns($1 \times 10^{-9}$s). Accordingly, the propagation time (delay) of the other ultrasonic wave B with respect to the frequency of the transmitted ultrasonic wave A, is within the above scope, and it is found that the other ultrasonic wave B does not have the bad influence on the amplitude of the transmitted ultrasonic wave A.

In the ultrasonic sensor 1 as described above, it is preferable that the piezoelectric element 300 serves both as a transmitting apparatus to transmit the ultrasonic wave and a receiving apparatus to receive the reflected echo signal. According thereto, it is possible to provide the ultrasonic sensor 1 which is advantageous for miniaturization. However, the transmitting apparatus to transmit the ultrasonic wave, and the receiving apparatus to receive the reflected echo signal, may be separately included.

Figure 7:
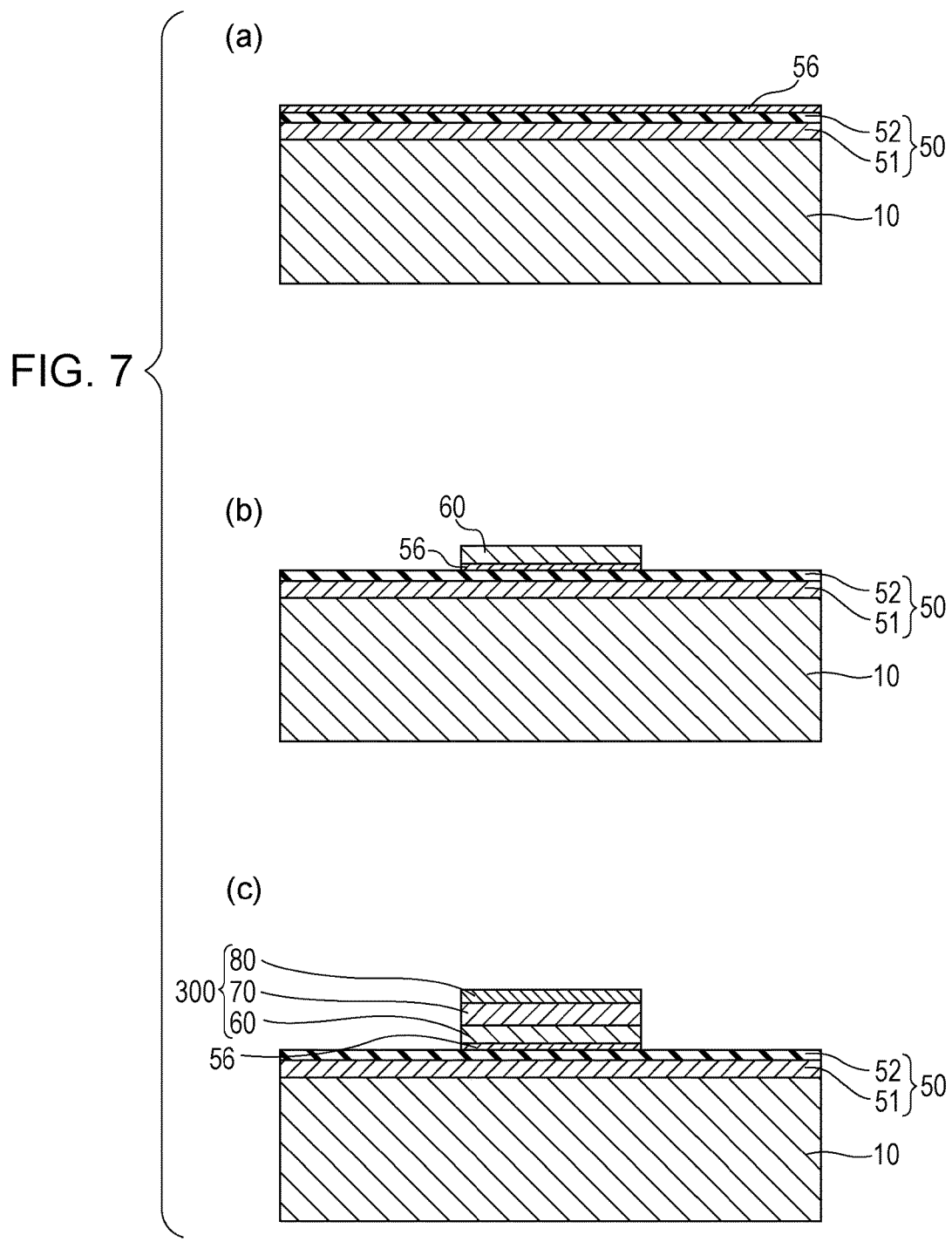
FIGS. 7(a)-(c) are diagrams describing a manufacturing example of the ultrasonic sensor according to Embodiment 1.
Figure 8:
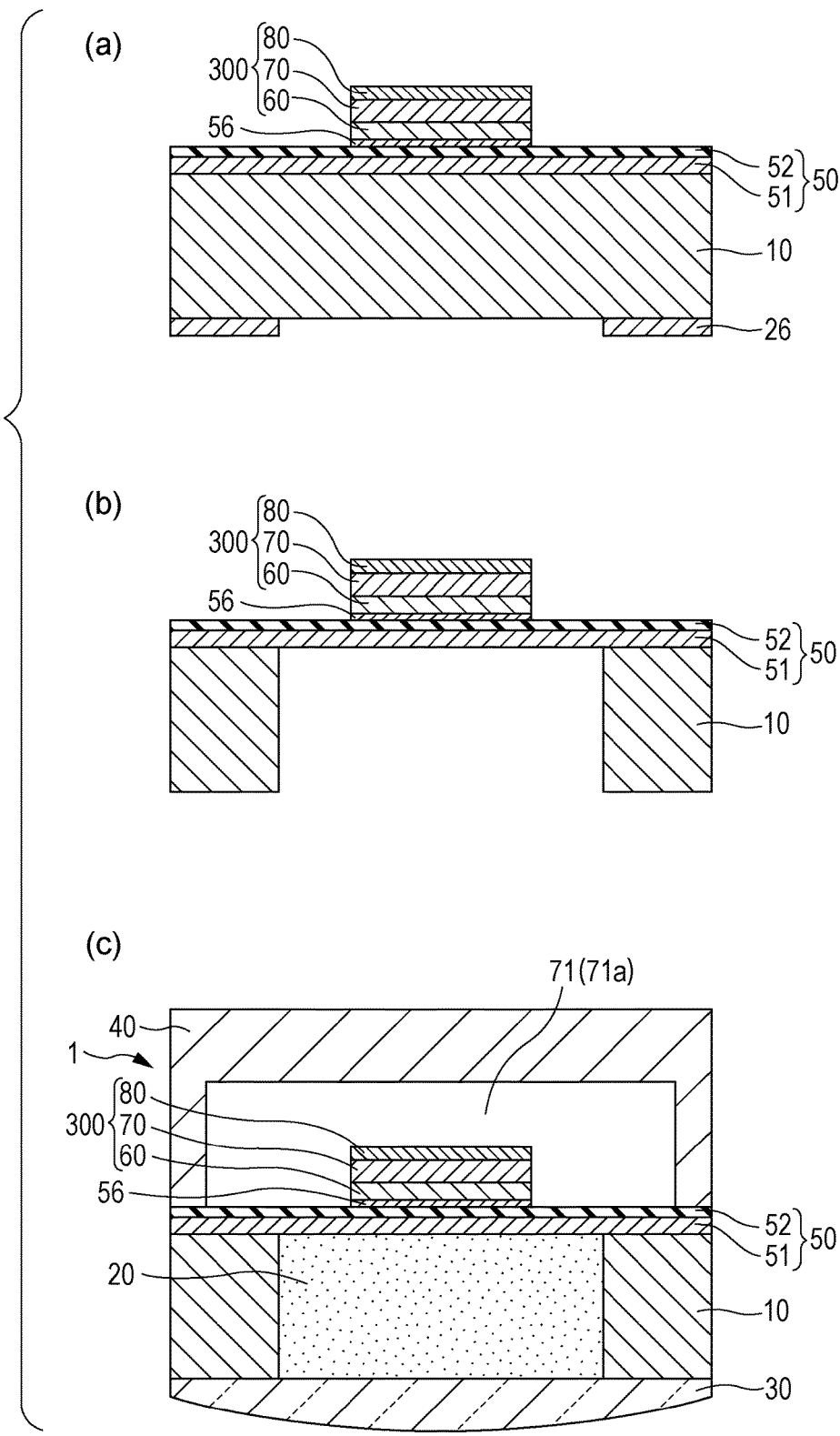
FIGS. 8(a)-(c) are diagrams describing the manufacturing example of the ultrasonic sensor according to Embodiment 1.

Next, an example of a method for manufacturing the ultrasonic sensor of the embodiment, will be described with reference to FIGS. 7 and 8. FIGS. 7 and 8 are cross-sectional views describing a manufacturing example of the ultrasonic sensor.

First, as shown in FIG. 7(a), after forming the vibration plate 50 on the substrate 10 by thermal oxidation, on the vibration plate 50, a film is formed with zirconium, and is thermally oxidized, for example, by a diffusion furnace of 500° C. to 1200° C., and the insulator film 52 which is made up of zirconium oxide, is formed. Therefore, on the insulator film 52, the adhesion layer 56 is formed by a sputtering method, the thermal oxidation or the like. Thereafter, as shown in FIG. 7(b), on the adhesion layer 56, the first electrode 60 is formed by the sputtering method, a vapor deposition method or the like, and the first electrode 60 and the adhesion layer 56 are patterned at the same time to have predetermined shapes.

Next, the piezoelectric material layer 70 is layered on the first electrode 60. For example, the piezoelectric material layer 70 may be formed using a chemical solution deposition (CSD) method in which a solution where a metal complex is dissolved and dispersed in a solvent, is coated and dried, and is further baked at a high temperature, and thereby, the piezoelectric material which is made up of metal oxide, is obtained. Furthermore, it is not limited to the CSD method, and for example, a sol-gel method, a laser abrasion ablation method, the sputtering method, a pulse laser deposition (PLD) method, a CVD method, an aerosol deposition method or the like, may be used. Thereafter, in the piezoelectric material layer 70, the second electrode 80 is formed by the sputtering method, the thermal oxidation or the like. Hereby, as shown in FIG. 7(c), on the adhesion layer 56, the piezoelectric element 300 which is made up of the first electrode 60, the piezoelectric material layer 70, and the second electrode 80, is formed.

Next, as shown in FIG. 8(a), a mask film 53 is formed in whole circumference on the substrate 10. Then, as shown in FIG. 8(b), by anisotropic etching (wet etching) the substrate 10 using an alkaline solution such as KOH through the mask film 53, the region which is opposed to the piezoelectric element 300 of the substrate 10, is removed.

Therefore, as shown in FIG. 8(c), the opposite side to the piezoelectric element 300 of the vibration plate 50, is inserted with the resin composition which becomes the acoustic matching layer 20, and the lens member 30 is joined onto the opposite side to the vibration plate 50 of the substrate 10. Thereafter, for example, with respect to an enveloping plate formation substrate which is made up of silicon materials, the enveloping plate 40 that is formed by etching the region which envelops the piezoelectric element 300, is joined to the vibration plate 50. As described above, the ultrasonic sensor 1 can be manufactured.

A measuring method using the ultrasonic sensor described above, has a process of reflecting other ultrasonic waves which are transmitted in the different direction from the transmitted ultrasonic wave transmitted to the measuring target side, and superimposing the other ultrasonic waves on the transmitted ultrasonic wave, by the reflection layer 71 that is provided on the opposite side to the opening section W of the vibration plate 50. The ultrasonic sensor 1 can be used as described above, and according thereto, the other ultrasonic waves which are transmitted in the different direction from the transmitted ultrasonic wave transmitted to the measuring target side, are superimposed on the transmitted ultrasonic wave, and the amplitude thereof can be enlarged.

Modification Example of Embodiment 1

In the above description, one embodiment of the invention is described, but a configuration thereof is not limited thereto.

Figure 9:
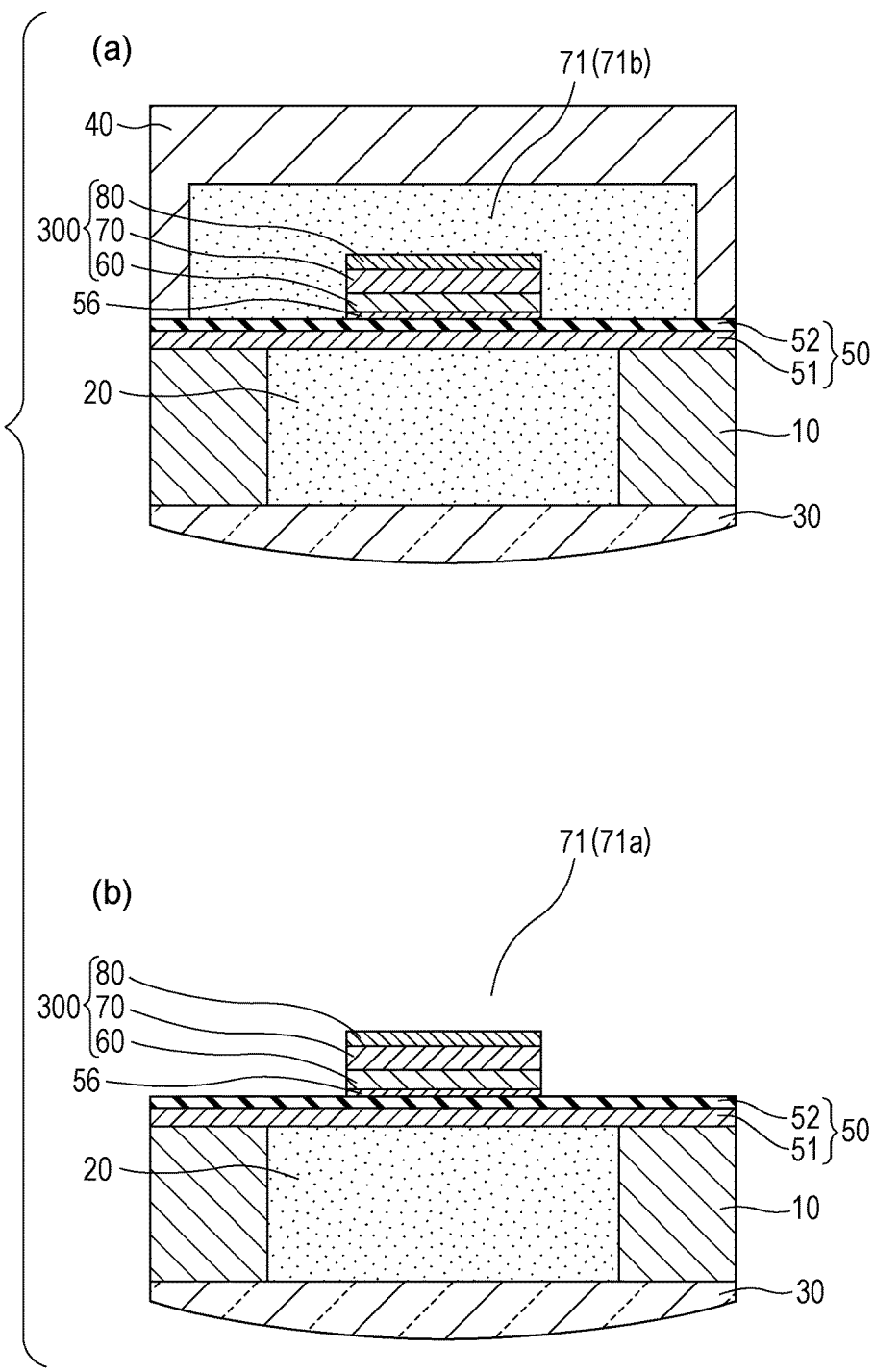
FIGS. 9(a) and (b) are diagrams illustrating a schematic configuration of an ultrasonic sensor according to a modification example of Embodiment 1.

For example, as shown in FIG. 9(a), the reflection layer can be configured to be made up of a resin composition layer 71b that is inserted between the piezoelectric element 300, and the enveloping plate 40 which is formed on the vibration plate 50 so as to envelop the piezoelectric element 300 and the space. According thereto, by changing the kind of the resin composition, it is possible to easily form the reflection layer of the different acoustic impedance. The inserted resin composition can be used by appropriately selecting the resin composition of which the acoustic impedance ratio to the piezoelectric element 300 is the predetermined value or more. As such resin composition layer, for example, vinyl chloride is exemplified, but it is not limited to the above example.

Moreover, as will be described in Embodiment 2 described below, for example, as shown in FIG. 9(b), the reflection layer 71 can be formed by omitting the sealing plate. Hereby, on basis of the impedance ratio at the interface between the air layer 71a as a reflection layer and the piezoelectric element 300, the transmitted ultrasonic wave can be reflected.

Embodiment 2

Figure 10:
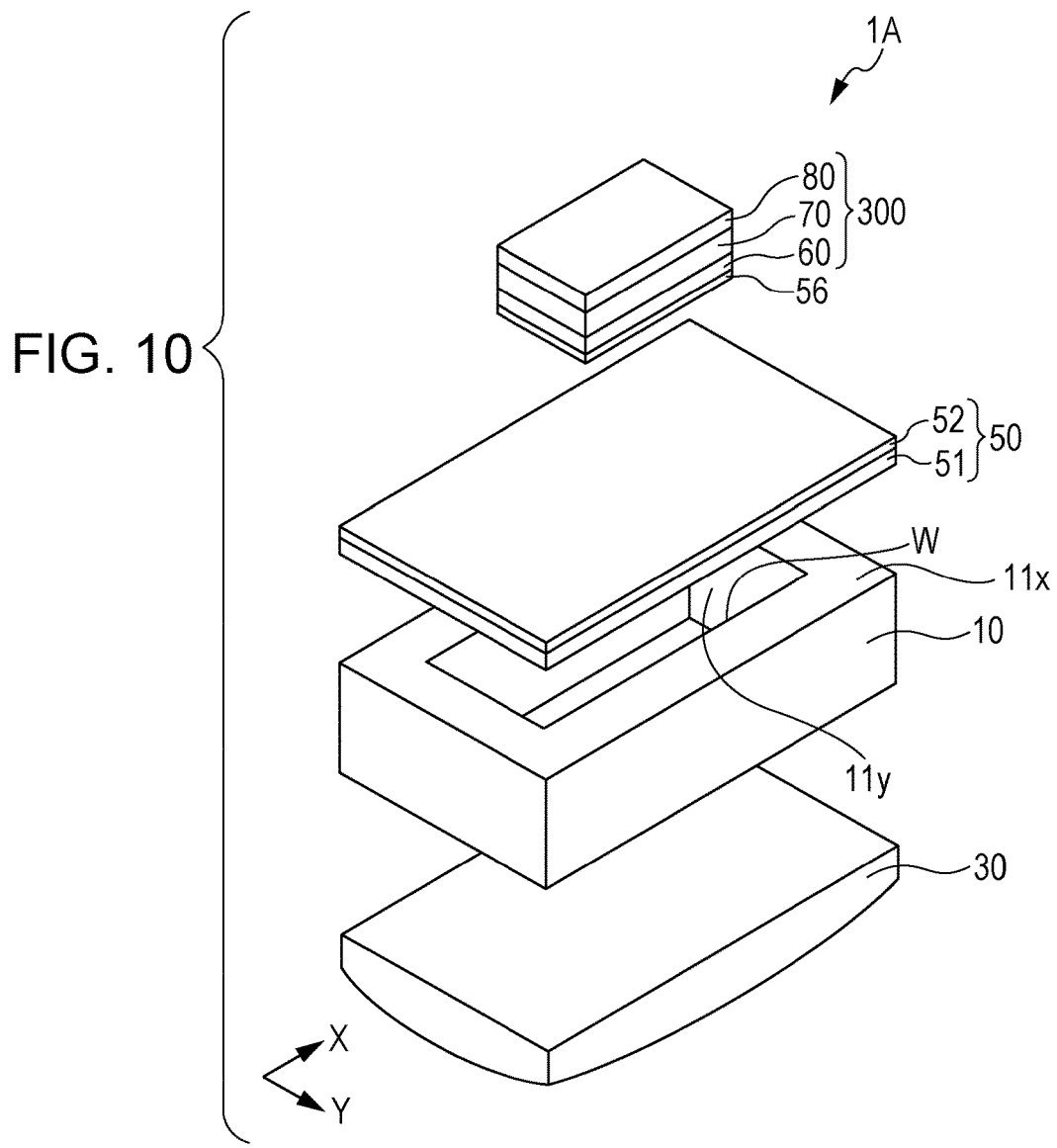
FIG. 10 is an exploded perspective view illustrating a schematic configuration of an ultrasonic sensor according to Embodiment 2.
Figure 11:
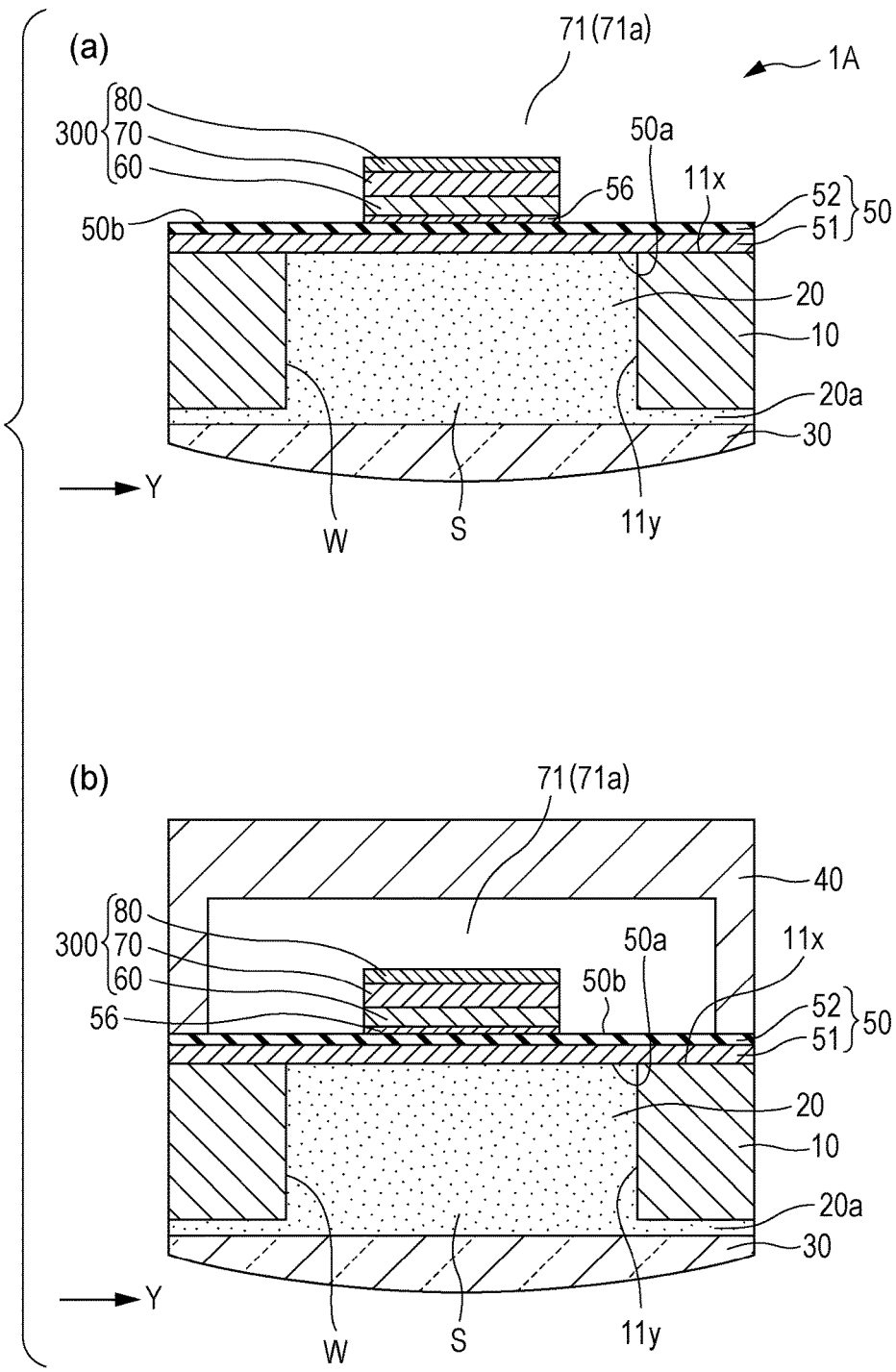
FIGS. 11(a) and (b) are cross-sectional views of the ultrasonic sensor according to Embodiment 2 and the modification example.

FIG. 10 is an exploded perspective view illustrating a schematic configuration of an ultrasonic sensor according to Embodiment 2 of the invention, and FIG. 11(a) is a cross-sectional view when the ultrasonic sensor shown in FIG. 10 is cut along a width direction. In addition, FIG. 11B is a modification example thereof. In drawings, the width direction in the ultrasonic sensor corresponds to the first direction X, and a direction orthogonal to the first direction X corresponds to a second direction Y.

As shown in drawings, an ultrasonic sensor 1A is substantially has the same configuration as Embodiment 1 described above. Therefore, the ultrasonic sensor 1A according to the embodiment also has the same function as Embodiment 1, and it is possible to obtain the same effect as Embodiment 1. Furthermore, in the embodiment, it is possible to apply the same materials, structures, and methods as Embodiment 1. Similarly, the ultrasonic sensor 1 according to Embodiment 1 has same function as Embodiment 2 to be described below, and it is possible to obtain same effect as Embodiment 2. Furthermore, materials, structures, and methods to be described in the following Embodiment 2 can be applied to Embodiment 1. In addition, in the embodiment, the same reference numerals as Embodiment 1 are used in parts being common to above-described Embodiment 1, and the description thereof will be partially omitted.

The ultrasonic sensor 1A according to the embodiment is configured of a minimum unit where there is one opening section W and the piezoelectric element 300 similar to above-described Embodiment 1. The ultrasonic sensor 1A configured of such a minimum unit is advantageous for miniaturization. Although described in Embodiment 1, it is also possible to configure one sensor such that two or more sensors made up of the minimum unit (hereinafter, referred to as a "sensor unit") are arranged in parallel one-dimensionally in a width direction or a length direction, or a plurality of sensors are arranged in parallel two-dimensionally in a width direction or a length direction. When a plurality of sensor units are arranged in parallel one-dimensionally or two-dimensionally, it is also possible to connect individual units after configuring the individual units, but the substrate 10, the vibration plate 50, and the lens member 30 may be shared. It is possible to appropriately select the first electrode 60 or the second electrode 80 as a common electrode, depending on a convenience of the drive circuit or the wiring, or convenience of manufacturing.

The substrate 10 is attached to a second surface 50a of the vibration plate 50. The substrate 10 includes the opening section W. The opening section W is provided at a position facing the piezoelectric element 300. The substrate 10 includes a first wall surface 11x parallel to the second surface 50a of the vibration plate, and a second wall surface 11y orthogonal to the second surface 50a of the vibration plate. The first wall surface 11 is joined with the second surface 50a of the vibration plate 50. The second wall surface 11y partitions the opening section W. As the substrate 10, for example, a substrate capable of forming the opening section W from one surface side by etching, as one example, a silicon (Si) single crystal substrate can be used. In addition, as the vibration plate 50, a plate capable of displacing thereof by bending and deformation of the piezoelectric element 300, as one example, a plate configured as the elastic film 51 which is made up of silicon dioxide ($SiO_2$) can be used. In the embodiment, as the vibration plate 50, a plate in which the insulator film 52 which is made up of zirconium oxide or the like is further formed on the elastic film 51. However, the insulator film 52 can be omitted.

In the embodiment, since the substrate 10 is attached to the second surface 50a of the vibration plate 50, that is, to a surface opposite side to the first surface 50b on which the piezoelectric element 300 is provided, the etching work or the process when the opening section W is formed on the substrate 10 or an angle of the connection portion between the vibration plate 50 and the substrate 10 is adjusted as a modification example to be described below is easy.

The piezoelectric element 300 is provided on the first surface 50b of the vibration plate 50. A region 71 around the piezoelectric element 300 (a region including an upper surface and side surfaces of the piezoelectric element 300) is set as an air layer 71a. For example, as shown in FIG. 11(a), the air layer 71a can be configured so as to expose the region 71 around the piezoelectric element 300. According to this, the air layer 71a can be constituted easily at a low cost. Accordingly, by setting the region 71 around the piezoelectric element 300 as the air layer 71a, the leakage current during driving of the piezoelectric element 300 can be remarkably reduced in comparison with a case where the acoustic matching layer is provided in the region around the piezoelectric element 300. Accordingly, it is possible to prevent adverse effects from a detection of a measuring target, as a result, it is possible to improve the detection accuracy including capability (distance resolution) to separate and identify the measuring target.

Furthermore, since the leakage current is remarkably reduced as described above, the ultrasonic sensor is an ultrasonic sensor 1A having excellent electrical safety. Accordingly, the ultrasonic sensor 1A can be suitably used as a pressure sensor or the like which is mounted on a liquid ejecting apparatus including a printer, needless to say, and can be suitably used for a medical device in situations averse to a leakage current in particular from a point of safety or the like, for example, an ultrasonic diagnostic apparatus, a sphygmomanometer, and a tonometer. In addition, according to the aspect, since it is possible to realize a configuration that the substrate 10 is connected to the opposite side to the piezoelectric element 300 of the vibration plate 50, the etching work or the process for adjusting the angle of the connection portion between the vibration plate 50 and the substrate 10 as a modification example to be described below is easy.

The air layer 71a is not limited to the configuration shown in FIG. 11(a). For example, as shown in FIG. 11(b), a space is secured in the region around the piezoelectric element 300 (the region including the upper surface and the side surfaces of the piezoelectric element 300), and the enveloping plate 40 may be attached on the first surface 50b of the vibration plate 50 so as to envelop the space and the piezoelectric element 300. In this case, the space serves a function as the air layer 71a. That is, the air layer 71a is formed in the region covered with the enveloping plate 40. According to this, similar to Embodiment 1, since the piezoelectric element 300 can be physically protected, it is possible to improve the detection accuracy including distance resolution. Therefore, it is possible to further improve the manufacturing strength of the ultrasonic sensor having excellent electrical safety. Furthermore, when the piezoelectric element 300 is configured as a thin film, availability for handling thereof can be improved, and thus, the ultrasonic sensor is easily manufactured and handled. Furthermore, the enveloping plate 40 can be configured by using a silicon-based material, for example, as same manner in the substrate 10 and the vibration plate 50, but the construction material can be appropriately selected.

Each layer of the first electrode 60, the piezoelectric material layer 70, and the second electrode 80 may be not in contact with each other, or other layers may be interposed therebetween. The same material as Embodiment 1 can be used in a material of the first electrode 60 or the second electrode 80.

The same material as Embodiment 1 can also be used in the piezoelectric material layer 70.

As described in Embodiment 1, in the complex oxide of the perovskite structure, the complex oxide which deviates from the composition of stoichiometry due to loss or excess, and the complex oxide where a portion of the element is substituted to other elements, are also included. That is, as long as the perovskite structure can be adopted, an inevitable deviation of the composition due to lattice mismatch, oxygen deficiency or the like, needless to say, and portion substitution of the element, are allowed.

The opening section W is provided at a position facing the piezoelectric element 300 by interposing the vibration plate 50. The opening section W is set as a passage region of an ultrasonic wave. The space S which is formed by the opening section W and the second surface 50a of the vibration plate 50 is filled with the acoustic matching layer 20 for propagating the ultrasonic wave. The acoustic matching layer 20 is configured by, for example, an acrylic-based or epoxy-based resin. In the embodiment, the acoustic matching layer 20 is configured by a resin type adhesive, and has a function as an adhesive for adhering the lens member 30 to the substrate 10. Here, it is configured such that the adhesive layer 20a by the acoustic matching layer 20 is interposed between the lens member 30 and the substrate 10. In Embodiment 1, similarly, it may be configured such that the adhesive layer 20a by the acoustic matching layer 20 is interposed therebetween. The lens member 30 is configured by a glass or a resin. Among two openings of the opening section W, one opening is closed by the second surface 50a of the vibration plate 50, and the other opening is closed by the acoustic matching layer 20 and the lens member 30.

In the acoustic matching layer 20, similarly to Embodiment 1, it is possible to prevent the rapid acoustic impedance change between the piezoelectric element 300 and the measuring target. When the acoustic matching layer 20 is provided between the piezoelectric element 300 and the measuring target, it is possible to reduce the changes in the acoustic impedance in the front and rear of the interface between the piezoelectric element 300 and the acoustic matching layer 20, and the interface between the acoustic matching layer 20 and the measuring target. Therefore, it is possible to reduce the reflection of the ultrasonic wave in these interfaces, the ultrasonic wave is efficiently propagated to the measuring target side, and the reflected ultrasonic wave is efficiently propagated to the vibration plate 50. In addition, in the embodiment, similar to the Embodiment 1, since the lens member 30 is provided thereto, three interfaces are present between the piezoelectric element 300 and the measuring target. The three interfaces are an interface between the piezoelectric element 300 and the acoustic matching layer 20 (a first interface), an interface between the acoustic matching layer 20 and the lens member 30 (a second interface), and an interface between the lens member 30 and the measuring target (a third interface), respectively. In the acoustic matching layer 20, the reflection of the ultrasonic wave can be reduced in the front and rear of the interface between the first interface and the second interface among the three interfaces. The reflection of the ultrasonic wave in the front and rear of the third interface is reduced by the lens member 30. In order to reduce the reflection of the ultrasonic wave in the second interface, it is preferable that the acoustic matching layer 20 and the lens member 30 are configured by materials having similar acoustic impedance values from each other.

In Table 1, an example of resin materials that can be used as the acoustic matching layer 20, and the acoustic impedances thereof is shown. The material that the acoustic impedance is gradually changed between the piezoelectric element 300 and the measuring target can be appropriately selected. In addition, within the scope of the invention as defined by the claims, the opening section W may be filled with the acoustic matching layer 20, and air bubbles may be mixed thereto. The materials of Table 1 can be used in the same manner as Embodiment 1.

TABLE 1

| Resin Material for Acoustic Matching Layer | Acoustic Impedance (Kg/m² sec) * 10⁻⁶ |
|---|---|
| Acrylic | 3.37 |
| Polycarbonate | 2.68 |
| PET | 2.97 |
| High-density polyethylene | 2.18 |
| Hard vinyl chloride | 3.2 |
| Polypropylene | 2.43 |
| ABS | 2.34 |
| Duracon | 3.35 |
| Silicone resin | 1.5 |

Similar to Embodiment 1, the piezoelectric element 300 is bent and deformed by the voltage application from a circuit (circuit 120 which is shown in FIG. 3 or the like) which is formed by a control unit which is configured with a known power supply apparatus or a known micro computer as the center. Since a tendency of the bent deformation of the piezoelectric element 300 is changed by the configuration materials, the thicknesses, arrangement, size or the like of the piezoelectric element 300 and the vibration plate 50, the tendency can be appropriately adjusted depending on an intended use and a use mode. Using a peculiar resonance frequency of each material, the resonance frequency is agreed with a frequency of a charge signal which is applied to the piezoelectric element 300, or is substantially agreed therewith, and the piezoelectric element 300 may be bent and deformed using the resonance. According to this, it is possible to transmit the ultrasonic wave having high strength by largely displacing the piezoelectric element 300 and the vibration plate 50 by using the resonance. In addition, by largely displacing the piezoelectric element 300 and the vibration plate 50 in accordance with a reflected ultrasonic wave from the measuring target, it is possible to obtain electric signals having high strength. According to this, since detection using the electrical signals having high strength becomes possible, it is possible to further improve the detection accuracy including distance resolution.

Figure 12:
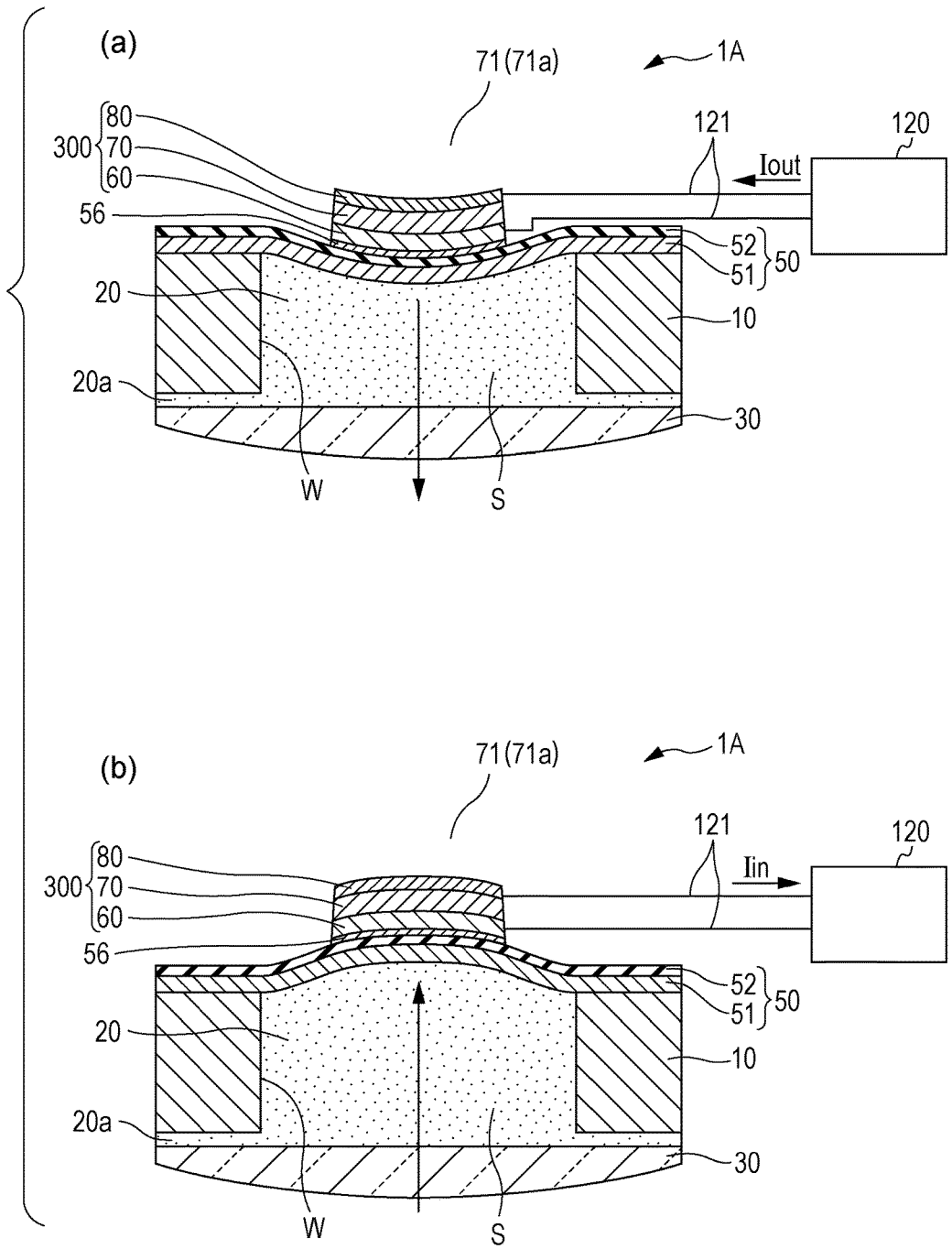
FIGS. 12(a) and (b) are schematic diagrams illustrating a motion of the ultrasonic sensor according to Embodiment 2.

FIG. 12(a) and FIG. 12(b) are schematic diagrams illustrating the motion of the ultrasonic sensor which is shown in FIG. 10. An electrical signal $I_{out}$ is supplied through the wiring 121 from the circuit 120, and thus the piezoelectric element 300 is bent and deformed with the piezoelectric material layer 70 which is interposed between the first electrode 60 and the second electrode 80 and is substantially a drive section, as a center thereof. According to this, the vibration plate 50 is displaced, the ultrasonic wave is generated in accordance with the displacement, and the ultrasonic wave is arrived to the measuring target by propagating the acoustic matching layer 20. FIG. 12(a) illustrates a process thereof, that is, a process of transmission of the ultrasonic wave.

In a case that there is the measuring target, the ultrasonic wave transmitted to the measuring target side, is reflected on the measuring target, and returns to the ultrasonic sensor 1A side. The ultrasonic wave which is reflected from the measuring target is incident on the vibration plate 50 by propagating the acoustic matching layer 20, and accordingly thereto, the vibration plate 50 and the piezoelectric element 300 are displaced. A charge is generated from the piezoelectric element 300 in accordance with the displacement, and is input to the circuit 120 through the wiring 121 as an electrical signal $I_{in}$. FIG. 12(b) illustrates a process thereof, that is, a process of reception of the ultrasonic wave. The position, shape, or the like of the measuring target is detected on the basis of intensities of the electrical signal $I_{in}$ and the electrical signal $I_{out}$ or timing therefor. Here, it is configured that the adhesive layer 20a by the acoustic matching layer 20 is interposed between the lens member 30 and the substrate 10. However, the function similar to Embodiment 1 is exhibited in such a configuration.

Embodiment 3

Next, an ultrasonic sensor according to Embodiment 3 of the invention will be described. In the ultrasonic sensor of the embodiment, it is possible to reduce the residual vibration of the acoustic matching layer, as a result, it is possible to further improve the detection accuracy including capability (distance resolution) to separate and identify the measuring target. Hereinafter, the description of the same parts as Embodiment 1 or Embodiment 2 will be omitted, and will be described the different parts mainly.

Figure 13:
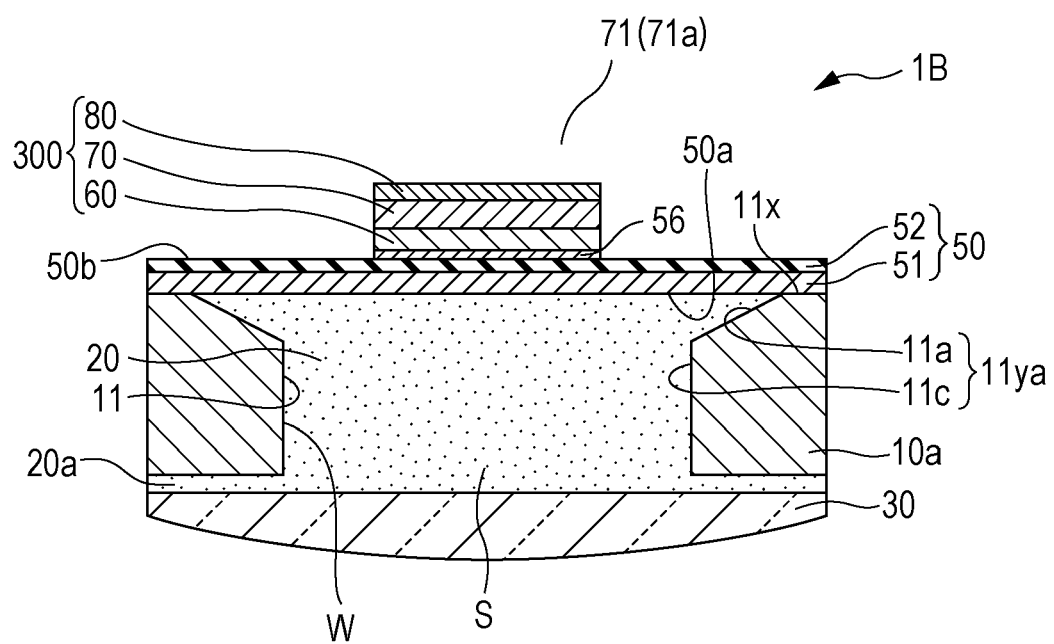
FIG. 13 is a cross-sectional view of an ultrasonic sensor according to Embodiment 3.

FIG. 13 is a cross-sectional view when an ultrasonic sensor 1B according to the embodiment is cut along the width direction, and FIG. 14(a) is an enlarged cross-sectional view illustrating a joint portion between the vibration plate 50 and the substrate 10 in FIG. 13. FIG. 14(b) is a plane view of a substrate 10a of the ultrasonic sensor 1B according to the embodiment when viewed from the first wall surface 11x side. The FIG. 14(c) is a modification example thereof.

In Embodiment 2, the vibration generated by the drive of the piezoelectric element 300 is residual in the acoustic matching layer 20, in some cases. When the vibration is residual for a long period of time, since the vibration mutually interferes with the ultrasonic wave which is reflected from the measurement target, it is difficult to accurately detect the reflected ultrasonic wave. Accordingly, it is preferable that the residual vibration is sufficiently reduced. In the embodiment, in the joint portion between the vibration plate 50 and the substrate 10a, the problem of the residual vibration is reduced by adjusting the angle of the substrate 10a surface. In the ultrasonic sensor 1B according to the embodiment, the configuration of a wall surface of the substrate 10a, specifically, the configuration of the wall surface of the joint portion with the vibration plate 50 is different from the configuration of Embodiment 1 or Embodiment 2. For the rest, it is same as in Embodiment 2. According to the ultrasonic sensor 1B, the same reference numerals are used in the same configuration as the embodiments described above, and the description thereof will not be repeated.

In the substrate 10 of Embodiment 2, as shown in FIG. 11(a) and FIG. 11(b), the second wall surface 11y partitioning the opening section W is configured of only the wall surface (the second wall surface 11y) perpendicular to the second surface 50a of the vibration plate. However, as shown in FIG. 13 and FIG. 14(a), in the ultrasonic sensor 1B according to the embodiment, an inclined wall 11a is provided on the joint portion between the vibration plate 50 and the substrate 10a. That is, the substrate 10a includes the first wall surface 11x which is joined to the vibration plate 50 and a second wall surface 11ya partitioning the opening section W. The second wall surface 11ya includes the inclined wall 11a and a vertical wall 11c. The first wall surface 11x is parallel with the second surface 50a of the vibration plate 50. Among the two walls constituting the second wall surface 11ya (the inclined wall 11a and the vertical wall 11c), the vertical wall 11c is perpendicular to the second surface 50a of the vibration plate 50. The inclined wall 11a is inclined to the first wall surface 11x and the vertical wall 11c. That is, the inclined wall 11a is not parallel with the first wall surface 11x and the vertical wall 11c, and is not perpendicular to the first wall surface 11x and the vertical wall 11c. An angle θ formed by the inclined wall 11a and the second surface 50a of the vibration plate 50 is equal to or greater than 90 degrees.

The inclined wall 11a is provided on the second wall surface 11ya partitioning the opening section W, and the angle θ formed by the inclined wall 11a and the second surface 50a of the vibration plate 50 is set to be equal to or greater than 90 degrees, therefore, it is possible to increase the cross-sectional area of the opening section W (a cross-sectional area in which the vibration plate 50 is cut along the surface parallel with the first surface 50b or the second surface 50a) toward the vibration plate 50 side. According to the two openings in the opening section W, when the area of an opening OPa on the vibration plate 50 side is set to "Sopa" and the area of an opening OPb on the other side (an opposite side to the vibration plate 50 side) is set to "Sopb", as shown in FIG. 14(b), it is possible to increase the area Sopa of the opening on the vibration plate 50 side more than the area Sopb of the opening on the other side. That is, when the second wall surface 11y is configured of only the vertical wall as Embodiment 2, and when the inclined wall 11a is provided as the embodiment with respect to the area of the opening on the vibration plate 50 side is set to "Sopb", the area of the opening on the vibration plate 50 side is set to be "Sopa". Therefore, the connection area between the vibration plate 50 and the acoustic matching layer 20 is increased. Accordingly, it is possible to reduce the area in which the displacement of the vibration plate 50 is restrained by the substrate 10, and to increase the operating region of the vibrating plate 50. By increasing the contact area between the vibration plate 50 and the acoustic matching layer 20, and increasing the operating region of the vibrating plate 50, it is possible to suitably absorb a residual vibration by the vibration plate 50, even if the residual vibration is generated in the acoustic matching layer 20. That is, the acoustic matching layer 20 is configured to exhibit a function as a so-called damper, therefore, it possible to reduce the residual vibration in the acoustic matching layer 20. As a result, it is possible to further improve the detection accuracy including distance resolution.

The structure in which the area Sopa of the opening on the vibration plate 50 side is increased by providing the inclined wall 11a in this manner, is not limited to the examples shown in FIG. 13 and FIG. 14(a). FIG. 14(c) is a view illustrating a modification example of the embodiment. In the embodiment, the configuration of the wall surface of the substrate 10b, specifically, the configuration of the wall surface of the joint portion which is joined with the vibration plate 50 is different from the configuration of Embodiment 3. For the rest, it is same as in Embodiment 3. In this modification example, the same reference numerals are used in the same configuration as the embodiments described above, and the description thereof will not be repeated.

As shown in FIG. 14(c), the substrate 10b includes the first wall surface 11x which is joined with the vibration plate 50 and the second wall surface 11yb partitioning the opening section W. The second wall surface 11yb includes an inclined wall 11b and two vertical walls 11d and 11e. The first vertical wall 11d is provided so as to connect the first wall surface 11x and the inclined wall 11b. The inclined wall 11b is provided between the first vertical wall 11d and the second vertical wall 11e. The inclined wall 11b is provided so as to connect the first vertical wall 11d and the second vertical wall 11e. The first wall surface 11x is parallel with the second surface 50a of the vibration plate 50. Both of the first vertical wall 11d and the second vertical wall 11e are perpendicular to the second surface 50a of the vibration plate 50. The inclined wall 11b is inclined to the first wall surface 11x and the vertical walls 11d and 11e. That is, the inclined wall 11b is not parallel with the first wall surface 11x and the vertical walls 11d and 11e, and is not perpendicular to the first wall surface 11x and the vertical walls 11d and 11e. The angle θ formed by the inclined wall 11b and the second surface 50a of the vibration plate 50 is greater than 90 degrees.

In Embodiment 3 and the modification example thereof, the angle θ thereof is greater than 90 degrees, and is within 180 degrees. In a viewpoint to more reliably obtain easiness in a process and a reduction effect of the residual vibration, it is preferable that the angle is set in the range of about 95 degrees to 105 degrees. The second wall surface 11yb including the inclined wall 11a is suitably formed by a method advantageous for processing the opening section W having a relatively small aspect ratio is provided in parallel one-dimensionally or two-dimensionally (such as, various milling methods).

In addition, it is not necessary to provide the inclined wall 11a on the whole second wall surface 11yb. For example, as shown in FIG. 14(b), in a case of the opening section W having a rectangular sectional shape, the inclined wall may be provided on only the surface corresponding to any one side of the rectangle. In addition, when the ultrasonic sensor unit is provided in parallel one-dimensionally or two-dimensionally, only the opening section W of a part of the unit may be configured as shown in FIG. 14(a), FIG. 14(b), or FIG. 14(c).

Figure 15:
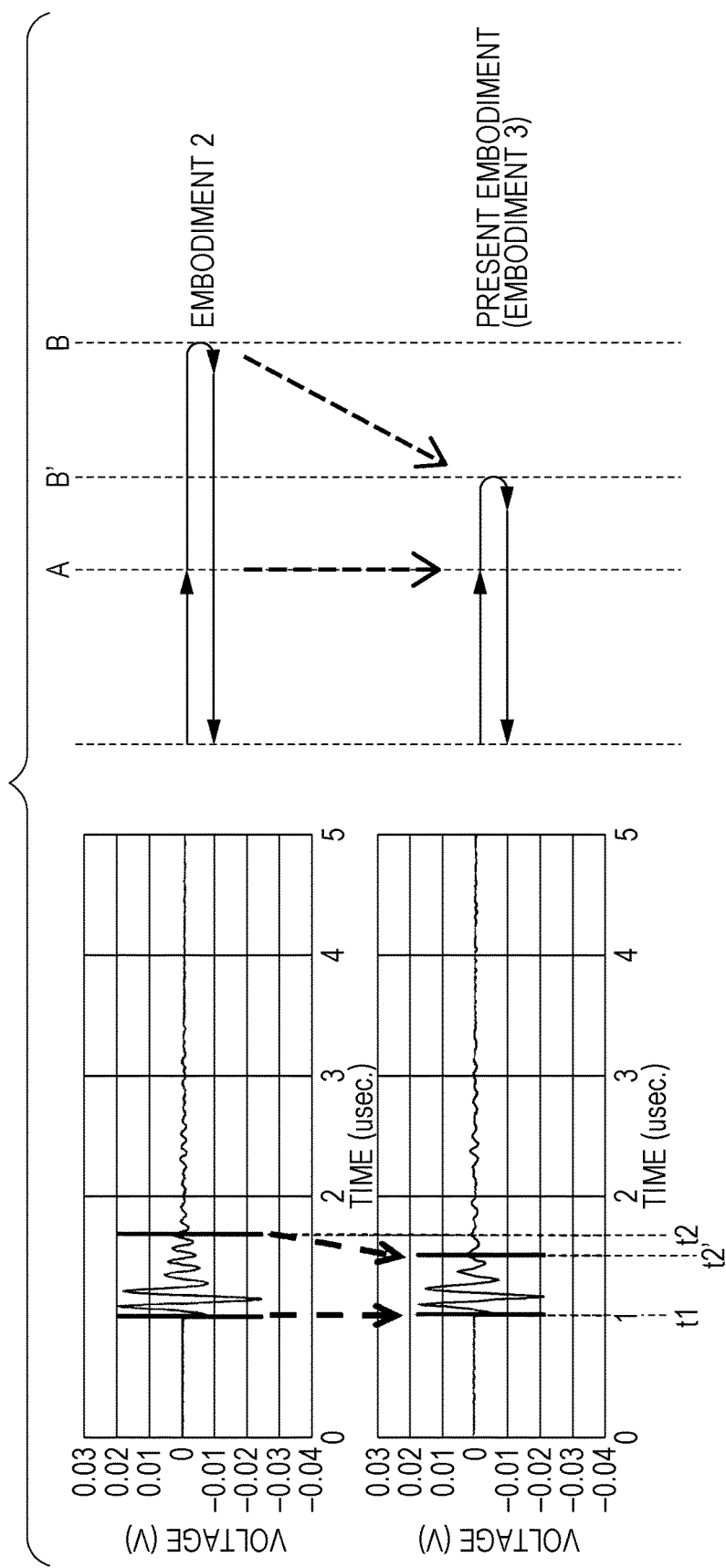
FIG. 15 is a diagram describing a residual vibration reducer function of the ultrasonic sensor according to Embodiment 3.

FIG. 15 is a diagram describing a transition of the residual vibration of the acoustic matching layer generated by the drive of the piezoelectric element, or a damper function of the acoustic matching layer caused by adjusting the angle θ thereof. In FIG. 15, a vertical axis of a wavelength represents amplitude (intensity of the ultrasonic wave), and a horizontal axis of the wavelength represents a time. For the comparison, the example of Embodiment 2 is shown in FIG. 15.

As shown in FIG. 15, in the embodiment, a period which is from a time point t1 that the vibration is generated in the acoustic matching layer 20 by the drive of the piezoelectric element 300 until a time point t2' that the vibration is reduced is shorter than a period which is from the time point t1 of generating the vibration until the time point t2 of reducing the vibration, in Embodiment 2. That is, the embodiment is more preferable in compared with Embodiment 2, in terms of the reduction of the residual vibration. However, in the embodiment, The decrease in the intensity of the ultrasonic wave with respect to Embodiment 2 it is not observed.

According to the embodiment, it is possible to improve the detection accuracy of the information related to the measuring target, in comparison with Embodiment 1 or Embodiment 2. For example, if the measuring targets A and B are not separated by a distance d or longer, the ultrasonic sensor 1A of Embodiment 2 cannot detect the targets by separating them, but the ultrasonic sensor 1B according to the embodiment can detect the measuring targets A and B by separating them, even when the measuring targets A and B are separated by a distance d or shorter.

Figure 16:
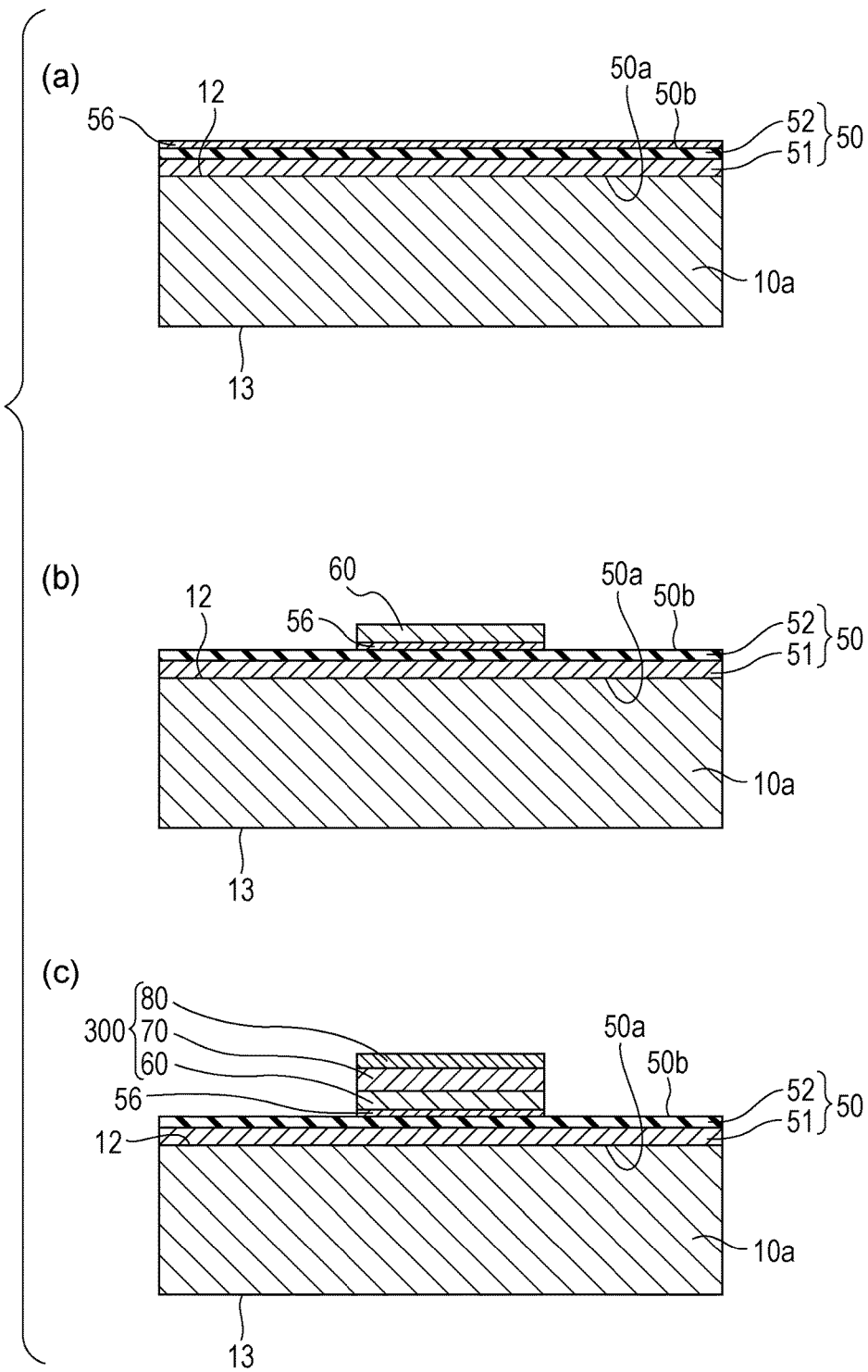
FIGS. 16(a)-(c) are diagrams describing a manufacturing example of the ultrasonic sensor according to Embodiment 3.
Figure 17:
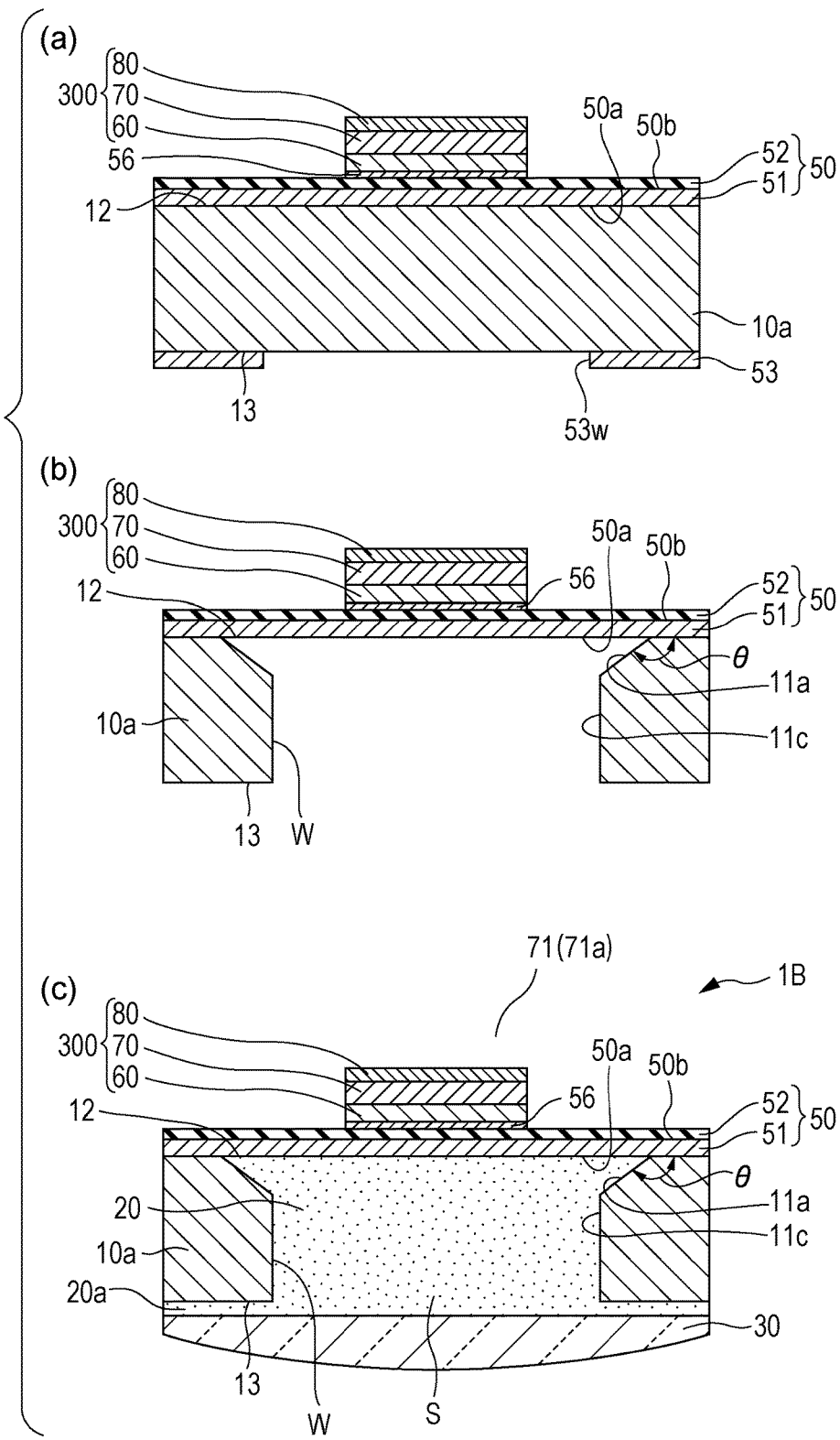
FIGS. 17(a)-(c) are diagrams describing a manufacturing example of the ultrasonic sensor according to Embodiment 3.

Next, an example of a method for manufacturing the ultrasonic sensor of the embodiment will be described with reference to FIGS. 16 and 17. FIGS. 16 and 17 are cross-sectional views illustrating a manufacturing example of the ultrasonic sensor.

First, as shown in FIG. 16(a), after forming the vibration plate 50 on one surface 12 of the substrate 10a by thermal oxidation (an elastic film 51), on the vibration plate 50, an insulator film 52 is formed with zirconium, and is thermally oxidized, for example, by a diffusion furnace of 500° C. to 1200° C., and the insulator film 52 which is made up of zirconium oxide, is formed. Therefore, on the insulator film 52, the adhesion layer 56 is formed by a sputtering method, the thermal oxidation or the like. Thereafter, as shown in FIG. 16(b), on the adhesion layer 56, the first electrode 60 is formed by the sputtering method, a vapor deposition method or the like, and the first electrode 60 and the adhesion layer 56 are patterned at the same time to have predetermined shapes.

Next, the piezoelectric material layer 70 is layered on the first electrode 60. For example, the piezoelectric material layer 70 may be formed using a chemical solution deposition (CSD) method in which a solution where a metal complex is dissolved and dispersed in a solvent, is coated and dried, and is further baked at a high temperature, and thereby, the piezoelectric material which is made up of metal oxide, is obtained. Furthermore, it is not limited to the CSD method, and for example, a sol-gel method, a laser abrasion ablation method, the sputtering method, a pulse laser deposition (PLD) method, a CVD method, an aerosol deposition method or the like, may be used. Thereafter, in the piezoelectric material layer 70, the second electrode 80 is formed by the sputtering method, the thermal oxidation or the like. Hereby, as shown in FIG. 16(c), on the adhesion layer 56, the piezoelectric element 300 which is made up of the first electrode 60, the piezoelectric material layer 70, and the second electrode 80, is formed.

Next, as shown in FIG. 17(a), a mask film 53 is formed on a surface 13 which is opposite to a surface 12 on which the piezoelectric element 300 of the substrate 10 is formed. An opening 53W is provided on the mask film 53. As shown in FIG. 17(b), by anisotropic etching (wet etching) the substrate 10 using an alkaline solution such as KOH through the opening 53W of the mask film 53, the region which is opposed to the piezoelectric element 300 of the substrate 10, is removed. The region obtained by etching in this manner becomes to the opening section W. In the etching process of here, by subjecting an over-etching the substrate 10, the angle θ formed by the inclined wall 11a and the second surface 50a of the vibration plate 50 is adjusted. In such an adjustment of the angle, the various milling devices may be used.

As shown in FIG. 17(c), a resin type adhesive is injected to the opening section W. The resin type adhesive is injected more than the volume of the opening section W. The lens member 30 is attached to the surface 13 which is opposite to the vibration plate 50 of the substrate 10 by an adhesive which is filled in the opening section W and an adhesive overflowing from the opening section W. Thereafter, the enveloping plate 40 (refer to FIG. 11(b)) may be joined with the vibration plate 50 as necessary. For example, with respect to the sealing plate formation substrate which is made up of silicon materials, the enveloping plate 40 is formed by etching the region which envelops the piezoelectric element 300. The ultrasonic sensor 1A of Embodiment 2 or the ultrasonic sensor including the configuration of the modification example in FIG. 5(b) can be manufacture by the method same as the above method. In the embodiment and Embodiment 2 or the modification example, the shapes of the second wall partitioning the opening W are different from each other. The shape of the second wall is can be appropriately changed by controlling the etching of the substrate 10.

Other Embodiment

In the above description, one embodiment of the invention is described, but the configuration thereof is not limited thereto. For example, in the above-described aspect, it is described that the piezoelectric element 300 serves both as the transmitting apparatus to transmit the ultrasonic wave and the receiving apparatus to receive the reflected ultrasonic wave from the measuring target. However, it is not limited to the examples described above, and it is possible so as to configure the transmitting apparatus to transmit the ultrasonic wave and the receiving apparatus to receive the reflected echo signal, separately.

Furthermore, since the ultrasonic sensor which is one embodiment of the invention, can be used as various kinds of pressure sensors, it can be applied to a liquid ejecting apparatus such as a printer. FIG. 18 is a schematic diagram illustrating an example of an ink jet type recording apparatus (liquid ejecting apparatus).

In an ink jet type recording apparatus II which is shown in FIG. 18, in recording head units having an ink jet type recording head, cartridges 2A and 2B configuring an ink supply unit are detachably provided, and a carriage 3 on which the recording head units are mounted, is provided on a carriage shaft 5 which is attached to an apparatus main body 4, to freely move in an axis direction. For example, the recording head units are the units for ejecting black ink composition, and color ink composition, respectively.

Therefore, drive force of a drive motor 6 is transmitted to the carriage 3 through a plurality of gears which are not shown in the drawing, and a timing belt 7, and thereby, the carriage 3 on which the recording head units are mounted, moves along the carriage shaft 5. On the other hand, a transport roller 8 as a transport unit, is provided in the apparatus main body 4, and a recording sheet S which is a recording medium such as paper, is transported by the transport roller 8. Furthermore, the transport unit that transports the recording sheet S, is not limited to the transport roller, and may be a drum, a belt or the like.

In addition, the configuration of the ultrasonic sensor of the invention can be suitably applied to an ultrasonic motor, a piezoelectric transformer, a vibration-type dust removal device, a pressure-electric conversion machine, an ultrasonic wave transmitting machine, an acceleration sensor, or the like.

As described above, in the ultrasonic sensor of the invention, the configuration that the region 71 around the piezoelectric element 300 is set as the air layer 71*a* and capable of reducing the leakage current during driving of the piezoelectric element 300 remarkably, is adopted. Accordingly, the ultrasonic sensor can be suitably used for a medical device in situations averse to the leakage current in particular from a point of electrical safety or the like, for example, an ultrasonic diagnostic apparatus, a sphygmomanometer, and a tonometer.

In addition, in the ultrasonic sensor as described above, the configuration where the opposite side to the piezoelectric element 300 of the vibration plate 50, becomes the passage region of the ultrasonic wave which is transmitted toward the measuring target, and the echo signal from the measuring target, is employed, and the electrical region such as the electrode and the wiring, and the adhered and fixed region of each member, are kept away from the measuring target, and it is easy to prevent the contamination and the leakage current between the regions and the measuring target. Accordingly, the ultrasonic sensor can be suitably applied to the medical device hating the contamination and the leakage current in particular, for example, the ultrasonic diagnostic apparatus, the sphygmomanometer, and the tonometer.

The invention claimed is:

1. An ultrasonic sensor comprising:
   a substrate having an opening section;
   a vibration plate provided on the substrate so as to close the opening section;
   a piezoelectric element provided on a surface of the vibration plate on an opposite side to the opening section, the piezoelectric element having a first electrode, a piezoelectric material layer, and a second electrode; and
   a reflection layer provided in a space around the piezoelectric element on the surface of the vibration plate on an opposite side to the opening section, to reflect other ultrasonic waves which are transmitted in a different direction from a transmitted ultrasonic wave transmitted to a measuring target side on an interface between the piezoelectric element and the reflection layer, the vibration plate and the piezoelectric element having a thickness so as to superimpose other ultrasonic waves on the transmitted ultrasonic wave.

2. The ultrasonic sensor according to claim 1,
   wherein an acoustic impedance ratio of the reflection layer to the piezoelectric element is three times or more.

3. The ultrasonic sensor according to claim 1,
   wherein the reflection layer has acoustic impedance which is smaller than the acoustic impedance of the piezoelectric element.

4. The ultrasonic sensor according to claim 1,
   wherein the reflection layer is made up of an air layer that is formed between the piezoelectric element, and an enveloping plate which is formed on the vibration plate so as to envelop the piezoelectric element and the space.

5. The ultrasonic sensor according to claim 1,
   wherein the reflection layer is made up of a resin composition layer that is inserted between the piezoelectric element and an enveloping plate which is formed on the vibration plate so as to envelop the piezoelectric element and the space.

6. The ultrasonic sensor according to claim 1,
   wherein other ultrasonic waves that are reflected on the interface between the reflection layer and the piezoelectric element have a phase difference which is greater than 0 degree, and is 120 degrees or less, with respect to the transmitted ultrasonic wave.

7. The ultrasonic sensor according to claim 1,
   wherein the thickness of the piezoelectric element is 0.4 μm to 2.0 μm.

8. The ultrasonic sensor according to claim 1,
   wherein the thickness of the vibration plate is 0.5 μm to 3.0 μm.

9. An ultrasonic sensor comprising:
   a vibration plate including a first surface and a second surface;
   a piezoelectric element provided on the first surface of the vibration plate, the piezoelectric element including a first electrode, a piezoelectric material layer, and a second electrode;
   a substrate attached to the second surface of the vibration plate, the substrate including an opening section at a position facing the piezoelectric element;
   an acoustic matching layer provided in a space formed by the opening section and the second surface of the vibration plate, to propagate a first ultrasonic wave generated by driving the piezoelectric element; and
   an air layer provided in a region around the piezoelectric element,
   wherein the air layer is configured to reflect other ultrasonic waves which are transmitted in a different direction from the first ultrasonic wave transmitted to a measuring target side on an interface between the piezoelectric element and the air layer, and the vibration plate and the piezoelectric element have a thickness so as to superimpose the other ultrasonic waves on the first ultrasonic wave.

10. The ultrasonic sensor according to claim 9,
    wherein the substrate includes a first wall surface that is provided in parallel to the second surface of the vibration plate and is joined with the second surface, and a second wall surface partitioning the opening section,
    the second wall surface includes a vertical wall perpendicular to the first wall surface and an inclined wall that is provided between the first wall surface and the second wall surface and is inclined to the first and second wall surfaces, and
    an angle formed by the inclined wall and the second surface of the vibration plate is equal to or greater than 90 degrees.

11. The ultrasonic sensor according to claim 9, further comprising:

a circuit that transmits and receives drive signals to and from the piezoelectric element,
wherein the circuit transmits and receives the drive signals for resonating the piezoelectric element in a resonant mode.

12. The ultrasonic sensor according to claim 9, further comprising:
an enveloping plate enveloping the piezoelectric element and the air layer on the first surface of the vibration plate.

13. A measuring method using an ultrasonic sensor which includes a substrate in which an opening section is formed, a vibration plate provided on the substrate so as to close the opening section, and a piezoelectric element having a first electrode, a piezoelectric material layer, and a second electrode which are layered on the vibration plate, the method comprising:
reflecting other ultrasonic waves which are transmitted in a different direction from a transmitted ultrasonic wave transmitted to a measuring target side by a reflection layer provided on an opposite side to the opening section of the vibration plate; and
superimposing the other ultrasonic waves on the transmitted ultrasonic wave.

14. A method for manufacturing an ultrasonic sensor, the method comprising:
preparing a substrate;
forming a vibration plate including a first surface and a second surface on the substrate;
forming a piezoelectric element including a first electrode, a piezoelectric material layer, and a second electrode on the first surface of the vibration plate;
forming an opening section at a position facing the piezoelectric element of the substrate;
providing an acoustic matching layer propagating a first ultrasonic wave generated by driving of the piezoelectric element in a space formed by the opening section and the second surface of the vibration plate; and
setting a region around the piezoelectric element as an air layer,
wherein the air layer is configured to reflect other ultrasonic waves which are transmitted in a different direction from the first ultrasonic wave transmitted to a measuring target side on an interface between the piezoelectric element and the air layer, and the vibration plate and the piezoelectric element have a thickness so as to superimpose the other ultrasonic waves on the first ultrasonic wave.

15. The method for manufacturing an ultrasonic sensor according to claim 14,
wherein the forming of the opening section includes
forming a vertical wall by etching the substrate so as to be perpendicular to the second surface of the vibration plate, and
forming an inclined wall so as to be inclined to the second surface of the vibration plate and the vertical wall, and so as to be equal to or greater than 90 degrees of an angle with respect to the second surface.

16. The method for manufacturing an ultrasonic sensor according to claim 14, further comprising:
providing an enveloping plate enveloping the piezoelectric element and the air surface on the first surface of the vibration plate.

* * * * *